United States Patent
Bolognesi et al.

(10) Patent No.: US 6,586,174 B1
(45) Date of Patent: *Jul. 1, 2003

(54) SUPPRESSOR OF HIV-1 REPLICATION AND TRANSCRIPTION

(75) Inventors: Dani P. Bolognesi, Durham, NC (US); Chin-Ho Chen, Durham, NC (US); Michael Greenberg, Durham, NC (US); Kent Weinhold, Durham, NC (US); Simon F. Lacey, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/450,141

(22) Filed: Nov. 29, 1999

Related U.S. Application Data

(60) Division of application No. 08/486,810, filed on Jun. 7, 1995, now Pat. No. 5,994,054, which is a division of application No. 08/471,430, filed on Jun. 6, 1995, now Pat. No. 5,861,490, which is a continuation-in-part of application No. 08/038,387, filed on Mar. 29, 1993, now Pat. No. 5,627,023.

(51) Int. Cl.[7] .................................................. C12Q 1/70
(52) U.S. Cl. .......................................... 435/5; 435/7.24
(58) Field of Search .............................................. 435/5

(56) References Cited

U.S. PATENT DOCUMENTS

| 5,627,023 A | * | 5/1997 | Bolognesi et al. | ............. 435/5 |
| 5,861,490 A | | 1/1999 | Bolognesi et al. | |

OTHER PUBLICATIONS

Barre–Sinoussi F, Chermann JC, Rey F, Nugeyre MT, Chamaret S, Gruest J, Dauguet C, Axler–Blin C, Vezinet–Brun F, Rouzioux C, Rozenbaum W, Montagnier L. Isolation of a T–lymphotropic retrovirus from a patient at risk for acquired immune deficiency syndrome (AIDS). Science. May 20, 1983;220(4599):868–71.

Chakrabarti S, Brechling K, Moss B. Vaccinia virus expression vector: coexpression of beta–galactosidase provides visual screening of recombinant virus plaques. Mol Cell Biol. Dec. 1985;5(12):3403–9.

Chen CH, Weinhold KJ, Bartlett JA, Bolognesi DP, Greenberg ML. CD8+ T lymphocyte–mediated inhibition of HIV–1 long terminal repeat transcription: a novel antiviral mechanism. AIDS Res Hum Retroviruses. Nov. 1993;9(11):1079–86.

Cullen BR, Greene WC. Regulatory pathways governing HIV–1 replication. Cell. Aug. 11,1989;58(3):423–6.

Dalgleish AG, Beverley PC, Clapham PR, Crawford DH, Greaves MF, Weiss RA. The CD4 (T4) antigen is an essential component of the receptor for the AIDS retrovirus. Nature. Dec. 20, 1984–Jan. 2, 1985;312(5996):763–7.

(List continued on next page.)

*Primary Examiner*—Laurie Scheiner
*Assistant Examiner*—Jeffrey S. Parkin
(74) *Attorney, Agent, or Firm*—Pennie & Edmonds LLP

(57) ABSTRACT

The present invention relates to a bioactive molecule, herein referred to as the $CD8^+$ suppressor molecule, that is produced by the $CD8^+$ subset of human T-lymphocytes and suppresses type-1 human immunodeficiency virus (HIV-1) replication through inhibition of viral transcription. The invention relates to isolation of clonal $CD8^+$ cells lines that produce the antiviral activity and the development of an assay system for detection of the antiviral activity. The clonal cell lines and the assay system, described herein, may be utilized to purify, characterize and clone the $CD8^+$ suppressor molecule. The $CD8^+$ suppressor molecule may have therapeutic applications for treatment of diseases associated with HIV-1 infection.

1 Claim, 15 Drawing Sheets

OTHER PUBLICATIONS

Figure 1:
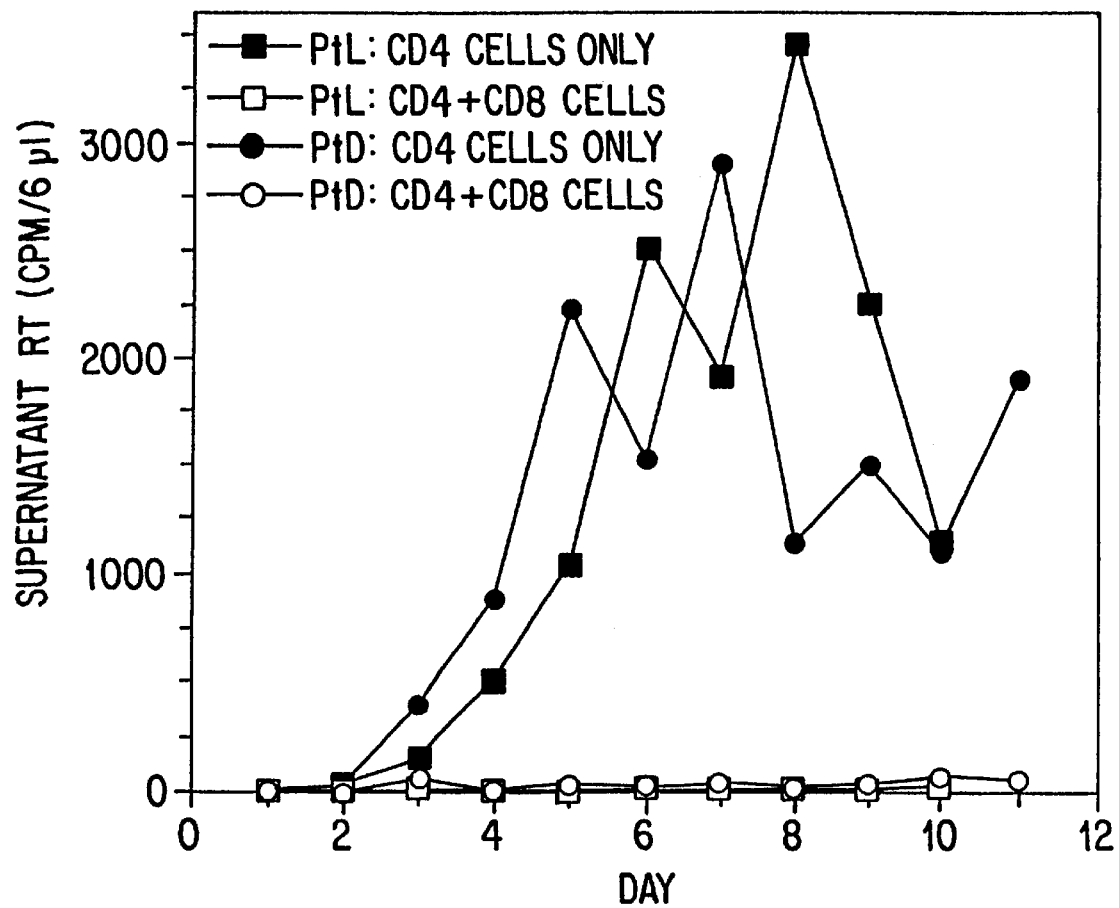

Earl PL, Hugin AW, Moss B. Removal of cryptic poxvirus transcription termination signals from the human immunodeficiency virus type 1 envelope gene enhances expression and immunogenicity of a recombinant vaccina virus. J Virol. May 1990;64(5):2448–51.

Flexner C, Broyles SS, Earl P, Chakrabarti S, Moss B. Characterization of human immunodeficiency virus gag/pol gene products expressed by recombinant vaccinia viruses. Virology. Oct. 1988;166(2):339–49.

Gallo RC, Salahuddin SZ, Popovic M, Shearer GM, Kaplan M, Haynes BF, Palker TJ, Redfield R, Oleske J, Safai B, et al. Frequent detection and isolation of cytopathic retroviruses (HTLV–III) from patients with AIDS and at risk for AIDS. Science. May 4, 1984;224(4648):500–3.

Goff S, Traktman P, Baltimore D. Isolation and properties of Moloney murine leukemia virus mutants: use of a rapid assay for release of virion reverse transcriptase. J Virol. Apr. 1981;38(1):239–48.

Jung JU, Trimble JJ, King NW, Biesinger B, Fleckenstein BW, Desrosiers RC. Identification of transforming genes of subgroup A and C strains of Herpesvirus saimiri. Proc Natl Acad Sci U S A. Aug. 15, 1991;88(16):7051–5.

Kannagi M, Masuda T, Hattori T, Kanoh T, Nasu K, Yamamoto N, Harada S. Interference with human immunodeficiency virus (HIV) replication by CD8+ T cells in peripheral blood leukocytes of asymptomatic HIV carriers in vitro. J Virol. Jul. 1990;64(7):3399–406.

Klatzmann D, Champagne E, Chamaret S, Gruest J, Guetard D, Hercend T, Gluckman JC, Montagnier L. T–lymphocyte T4 molecule behaves as the receptor for human retrovirus LAV. Nature. Dec. 20, 1984–Jan. 2, 1985;312(5996):767–8.

Maddon PJ, Dalgleish AG, McDougal JS, Clapham PR, Weiss RA, Axel R. The T4 gene encodes the AIDS virus receptor and is expressed in the immune system and the brain. Cell. Nov. 7, 1986;47(3):333–48.

Walker CM, Erickson AL, Hsueh FC, Levy JA. Inhibition of human immunodeficiency virus replication in acutely infected CD4+ cells by CD8+ cells involves a noncytotoxic mechanism. J Virol. Nov. 1991;65(11):5921–7.

Walker CM, Moody DJ, Stites DP, Levy JA. CD8+ T lymphocyte control of HIV replication in cultured CD4+ cells varies among infected individuals. Cell Immunol. Apr. 1, 1989;119(2):470–5.

Willey RL, Smith DH, Lasky LA, Theodore TS, Earl PL, Moss B, Capon DJ, Martin MA. In vitro mutagenesis identifies a region within the envelope gene of the human immunodeficiency virus that is critical for infectivity. J Virol. Jan. 1988;62(1):139–47.

* cited by examiner

SUPPRESSOR OF HIV-1 REPLICATION AND TRANSCRIPTION

This application is a division of Ser. No. 08/486,810 Jun. 7, 1995 U.S. Pat. No. 5,994,054 which is a division of Ser. No. 08/471,430 Jun. 6, 1995 U.S. Pat. No. 5,861,490 which is a continuation-in-part of Ser. No. 08/038,387 Mar. 29, 1993 U.S. Pat. No. 5,627,023.

1. INTRODUCTION

The present invention relates to a bioactive molecule, herein referred to as the CD8 suppressor molecule, that is produced by the CD8 subset of human T-lymphocytes and suppresses human immunodeficiency virus (HIV) replication through inhibition of viral transcription. The invention relates to isolation of clonal CD8 cells lines and/or the generation of permanently established transformed CD8 cell lines that produce the antiviral activity and the development of an assay system for detection of the antiviral activity. The clonal cell lines and the assay system, described herein, may be utilized to purify, characterize and clone the CD8 suppressor molecule. The CD8 suppressor molecule may have therapeutic applications for treatment of diseases associated with HIV infection.

2. BACKGROUND OF THE INVENTION

The type-1 human immunodeficiency virus (HIV-1) has been implicated as the primary cause of the slowly degenerate disease of the immune system termed acquired immune deficiency syndrome (AIDS) (Barré-Sinoussi, F. et al., 1983 Science 220:868–70; Gallo, R. et al. 1984, Science 224:500–3). Infection of the CD4+subclass of T-lymphocytes with the HIV-1 virus leads to depletion of this essential lymphocyte subclass which inevitably leads to opportunistic infections, neurological disease, neoplastic growth and eventually death. HIV-1 infection and HIV-1 associated diseases represent a major health problem and considerable attention is currently being directed towards the successful design of effective therapeutics.

HIV-1 is a member of the lentivirus family of retroviruses (Teich, N. et al., 1984 In RNA Tumor Viruses ed. R. Weiss, N. Teich, H. Varmus, J. Coffin CSH Press, pp. 949–56). The life cycle of HIV-1 is characterized by a period of proviral latency followed by active replication of the virus. The primary cellular target for the infectious HIV-1 virus is the CD4 subset of human T-lymphocytes. Targeting of the virus to the CD4 subset of cells is due to the fact that the CD4 cell surface protein acts as the cellular receptor for the HIV-1 virus (Dalgleish, A. et al., 2984, Nature 312:763–67; Klatzmann et al. 1984, Nature 312:767–68; Maddon et al. 1986 Cell 47:333–48).

After binding to the cell surface, the HIV-1 virion becomes internalized, and once inside the cell, the viral life cycle begins by conversion of the RNA genome into linear DNA molecules. This process is dependent on the action of the virally encoded reverse transcriptase. Following replication of the viral genome, the linear DNA molecule integrates into the host genome through the action of the viral integrase protein, thus establishing the proviral form of HIV-1.

During the early phase of proviral expression, transcription of the viral genome results in expression of regulatory proteins such as Tat, Nef and Rev. Transcriptional activation of the proviral DNA is mediated through the viral 5' LTR sequences (long terminal repeats). The initial low level of viral transcription is dramatically increased by the HIV encoded transactivator protein termed tat (transactivator protein) (Cullen, B. R. et al. 1989, Cell 58:423–26). The Rev protein promotes the transition from the early phase expression of regulatory proteins to late phase expression of structural proteins. Assembly of newly synthesized viral particles is followed by budding of virus particles from the cell membrane allowing the virus to infect new cells.

The HIV-1 virus is capable of establishing a latent state of infection for prolonged periods of time. Individuals infected with the human immunodeficiency virus may remain clinically healthy for long periods of time, with the estimated average length of the asymptomatic period between primary HIV infection and the progression to AIDS and increase in viral replication being approximately 8 to 10 years. Several possibilities have been proposed to explain the maintenance of the low levels of viral replication during this period of latency. It is generally believed that the humoral immune response to HIV-1 is not sufficiently protective against progression of the disease and attention has, therefore, turned to the possibility that the T-lymphocyte population of cells may directly inhibit HIV-1 replication.

A number of groups have recently noted that the CD8+ subset of T-lymphocytes have the ability to inhibit the replication of HIV-1 in vitro (Walker, C. M. et al., 1989, Cellular Immunology 119:470–475; Kannagi, M. et al. 1990, J. Virology 64:3399–3406; Walker, C. M. et al., 1991 J. Virology 65:5921–5927). For example, addition of CD8 cells to naturally HIV-1 infected CD4 cell cultures was found to inhibit the replication of HIV-1 in the infected cultures in a dose dependent manner. (Ref. supra). Furthermore, the inhibitory effect is not dependent on cell-cell contact as an inhibitory effect is observed across a semi-permeable membrane suggesting that the CD8 suppressor activity is a soluble inhibitor of HIV-1 replication. (Ref. supra). To date, the molecular identity of the CD8 suppressor molecule, or a combination of factors, as well as the mechanism by which it exerts its antiviral effect remains undefined.

3. SUMMARY OF THE INVENTION

The present invention relates to a soluble molecule secreted by the CD8+ subclass of T-lymphocytes and to the ability of that molecule to markedly inhibit HIV viral replication. The invention further relates to the observation that the mechanism by which the suppressor molecule exerts its antiviral activity is at the level of inhibition of viral gene expression from the viral LTR promoter.

In a principle embodiment, the invention is directed to an assay system to be used for detection of the HIV inhibitory activity, whereby the HIV LTR sequence is cloned adjacent to a reporter gene such as the CAT gene. In such an assay system, the presence of the suppressor molecule may be determined by measuring the levels of reporter gene product.

The present invention relates to the isolation and characterization of CD8+ cell clones that produces the antiviral activity. The invention further relates to the generation of permanently established CD8+ cell lines that produce the antiviral activity. Such cell lines may be generated by transferring cellular or viral genes capable of transformation or immortalization into CD8+ cells.

CD8+ clonal cells and/or CD8+ permanently established cell lines that produce the antiviral activity of interest may be advantageously used for large scale isolation and characterization of the suppressor molecule and/or as a source of mRNA for construction of cDNA libraries that may be used for cloning the suppressor molecule. The invention also relates to the use of the suppressor molecule in the treatment of HIV-infection.

4. DESCRIPTION OF THE FIGURES

FIG. 1. CD8+ Cells from HIV-1 Seropositive Individuals Suppresses virus production.

Figure 2:
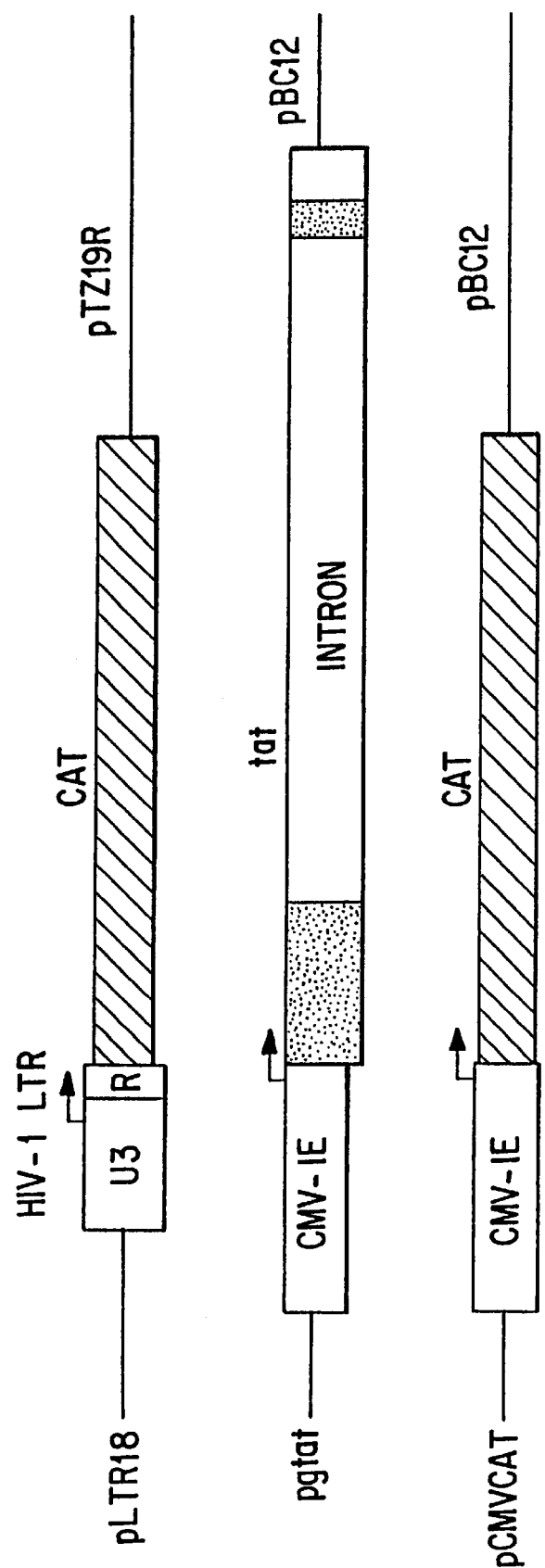

FIG. 2. Plasmid constructs used in HIV-1 LTR transcription assays.

Figure 3:
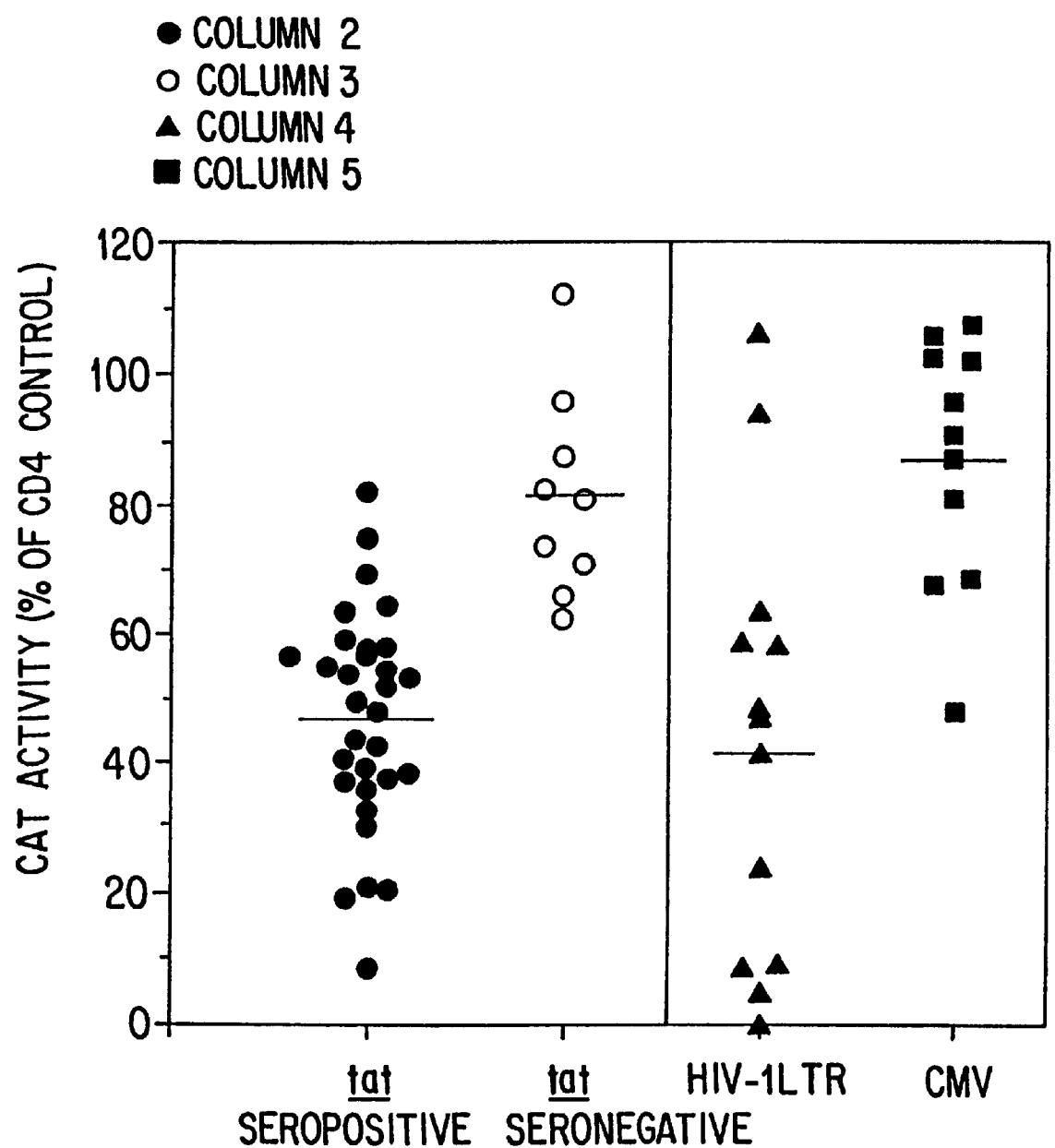

FIG. 3. CD8+ Cells from HIV-1 infected individuals suppress HIV-1 LTR transcription. Data are plotted for CAT activity in cultures containing autologous CD8+ cells compared to the activity measured in cultures derived from the same transfection containing autologous CD4 cells. Horizontal lines are drawn to indicate the means of each population.

Figure 4:
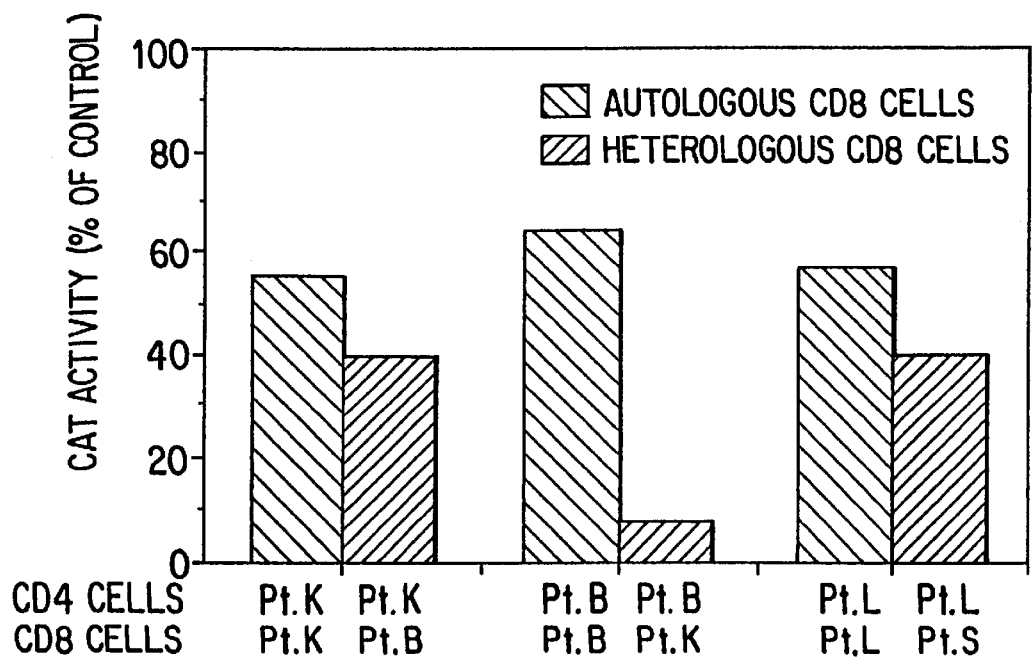

FIG. 4. CD8+ cells suppress Tat-mediated transcription in heterologous CD4 cells. Data are plotted for CAT activity in cultures containing autologous or heterologous CD8+ cells compared to the activity measured in cultures derived from the same transfection containing autologous CD4 cells.

Figure 5:
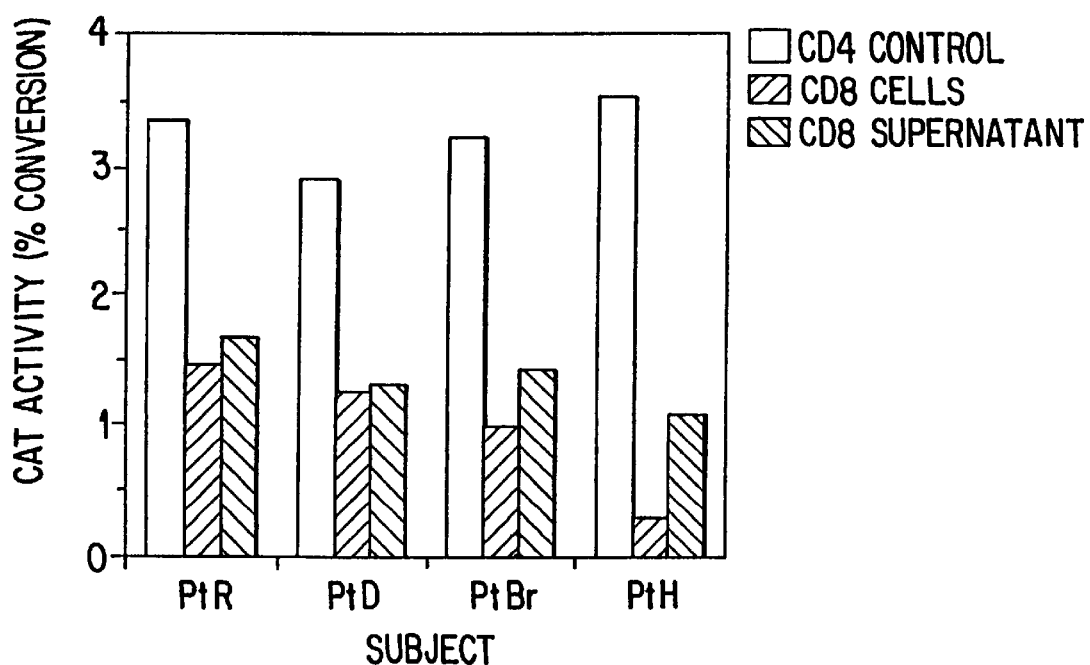

FIG. 5. A soluble factor from CD8+ cells inhibits Tat-mediated transcription. CAT activity was measured in cultures containing autologous CD4 cells, cultures containing autologous CD8+ cells and cultures containing autologous CD8+ cell conditioned medium. Each data set from an individual subject was derived from a single transfection. CAT activity is expressed as percent conversion, each assay was based on $5 \times 10^6$ transfected CD4 cells.

Figure 6:
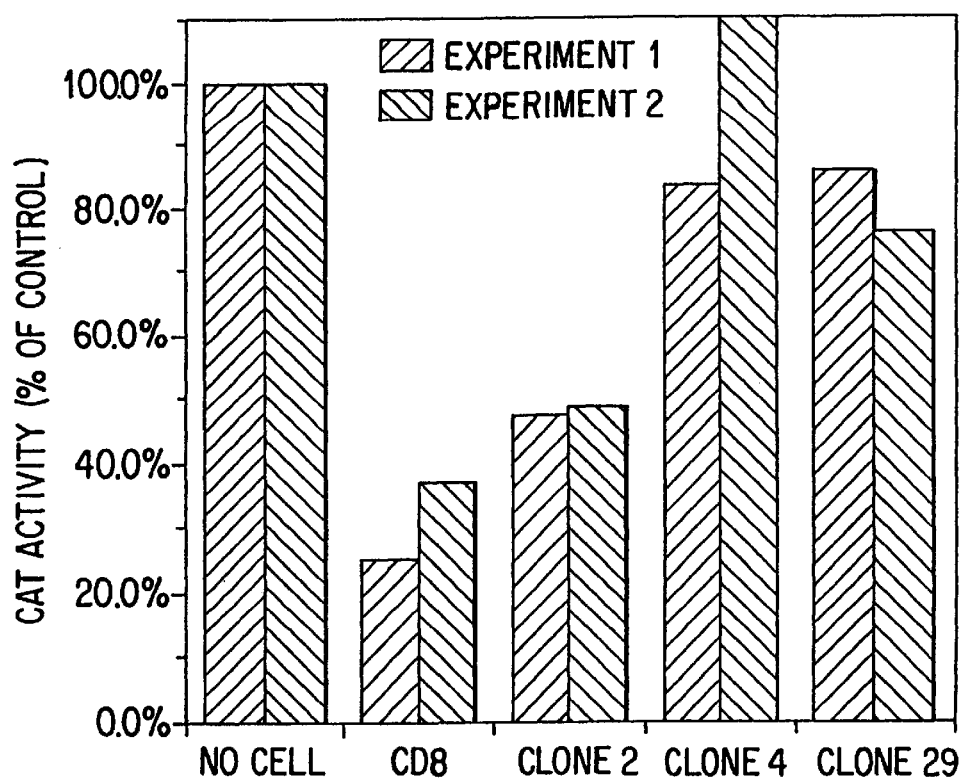

FIG. 6. HIV transcriptional inhibition is expressed by a primary CD8+ cell clone.

Figure 7A:
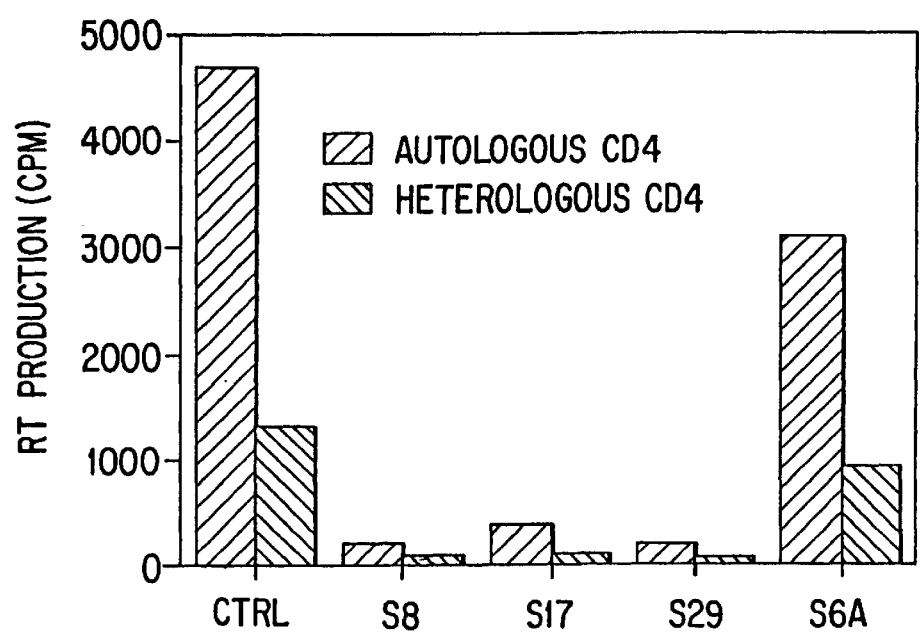
Figure 7B:
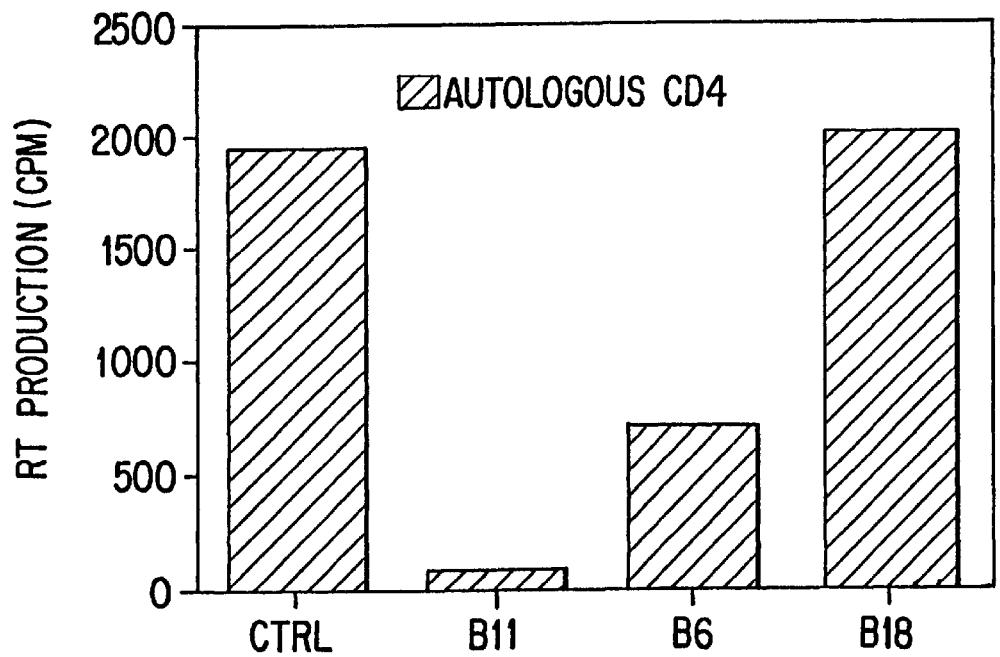
Figure 7C:
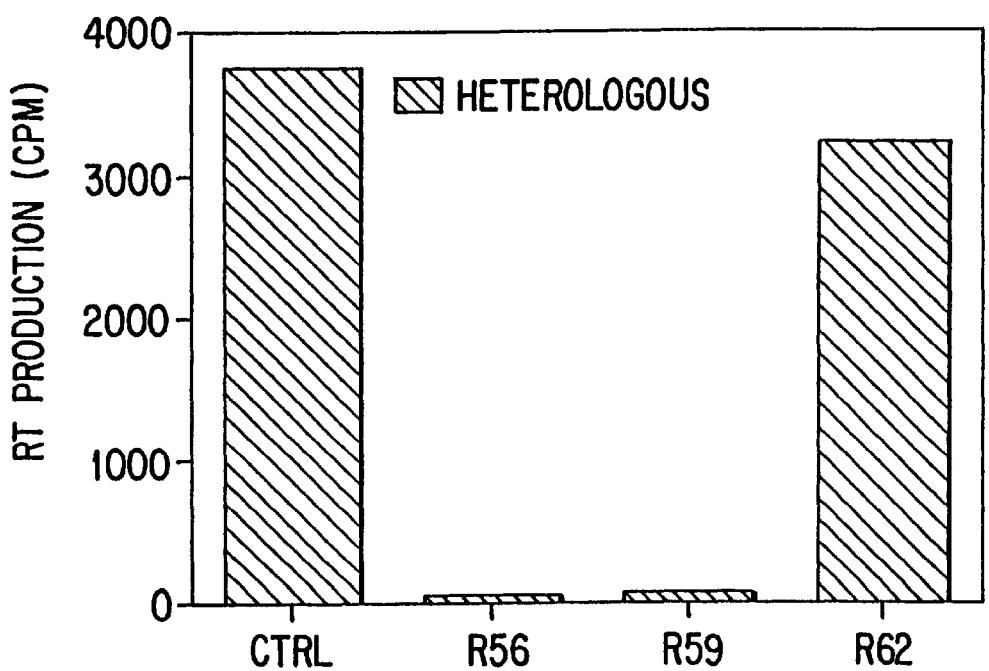

FIG. 7. Anti-HIV-1 activity of CD8+ clones in autologous and heterologous co-culture screening assays. Controls represent RT production of infected CD4 in the absence of other cells. (A) Clones from patient S were screened against both heterologous, acutely infected CD4 cells and autologous, naturally infected CD4 cells. The data shown was collected on day 6 of assay. (B) Clones from patient B were screened against autologous, naturally infected CD4 cells. Data shown was also collected on day 6. (C) Clones from patient R were screened against heterologous, naturally infected CD4 cells. Data shown was collected on day 3 of assay.

Figure 8:
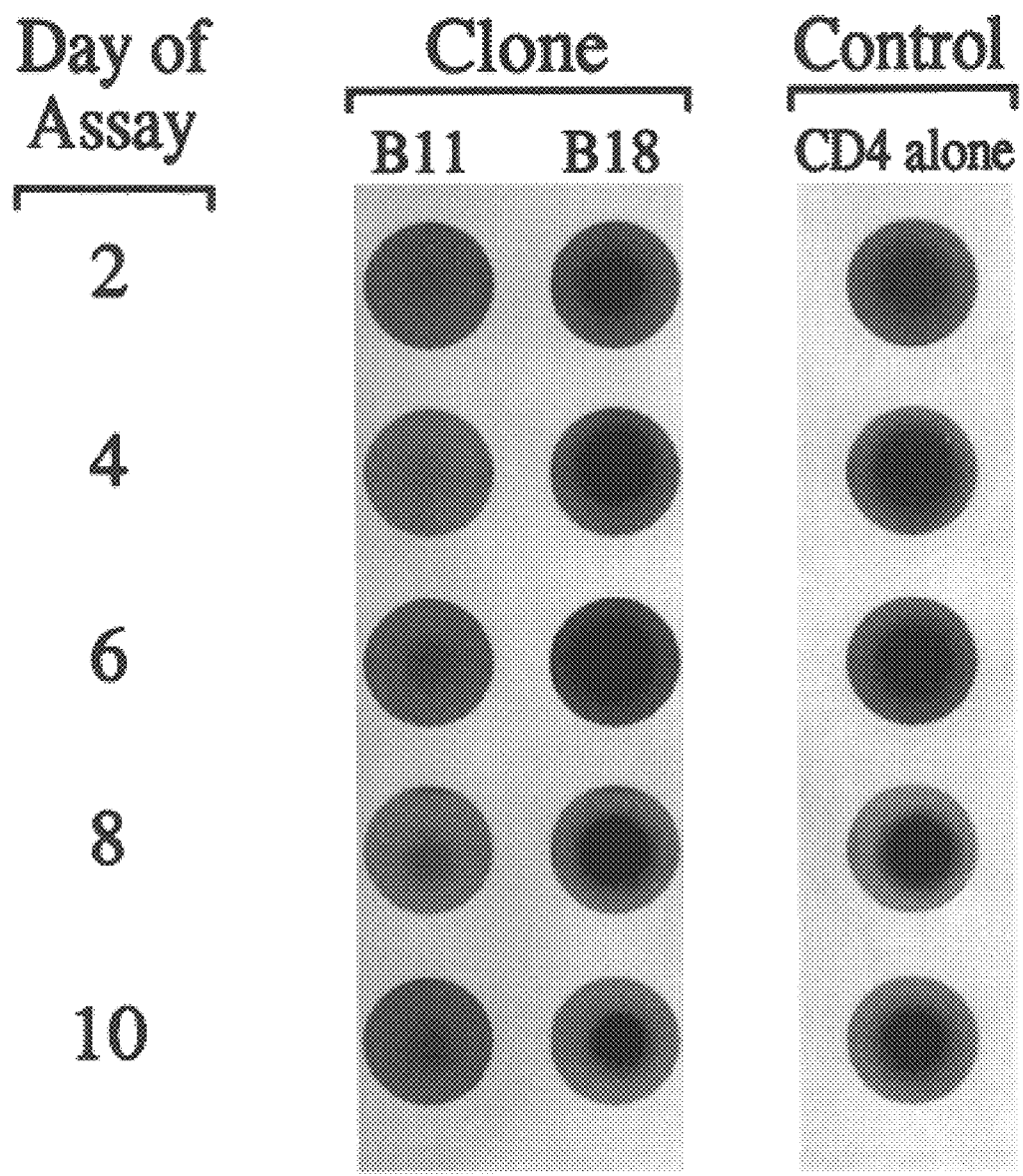

FIG. 8. Autoradiograph of RT assay showing anti-HIV-1 activity of clone B11 compared to non-active clone B18 and to acutely infected CD4 cells alone. The E:T ratio at the commencement of the assay was 2:1.

Figure 9A:
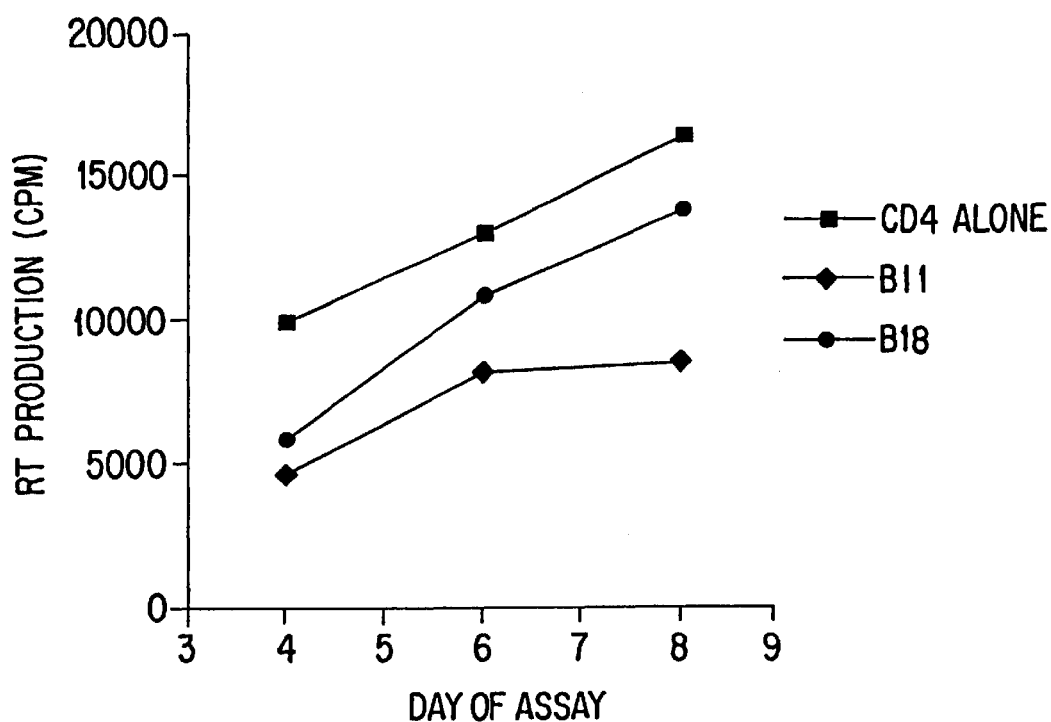
Figure 9B:
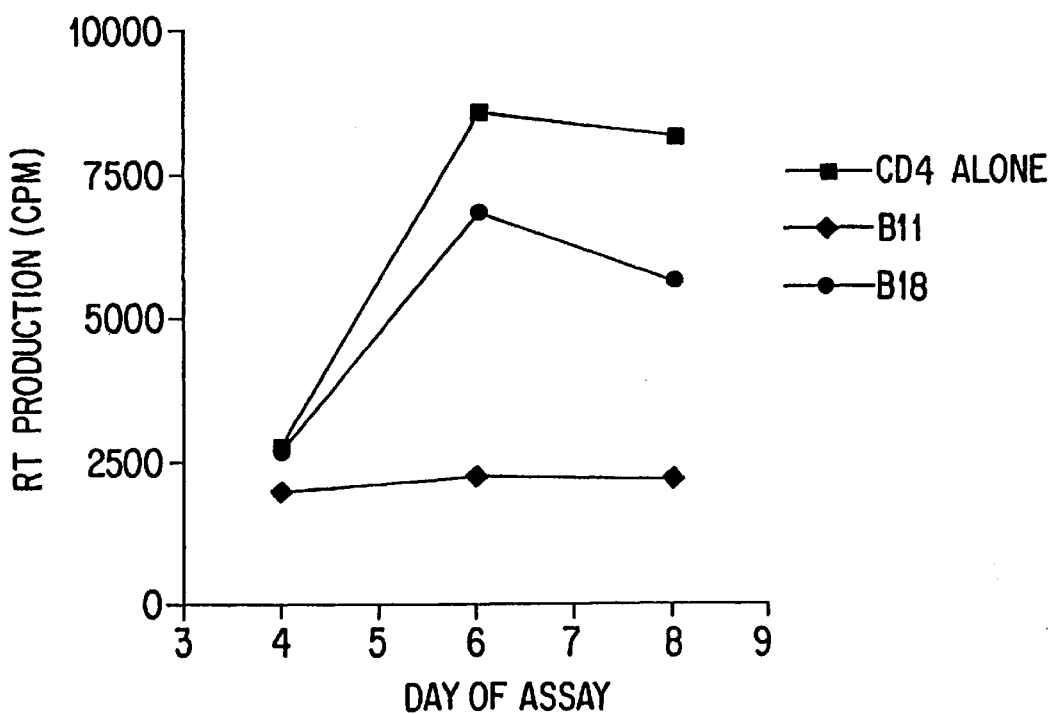

FIG. 9. CD8+ clones from Patient B were separated from acutely infected CD4 targets by a filter with 0.4 $\mu$m pores in the context of transwell plates (Costar). A 4:1 E:T ratio was employed. Supernatant was sampled for RT activity at day 4, 6, and 8 after culture as shown. The second graph shows the results of a parallel coculture experiment. A 2:1 E:T ratio was employed. The effectors of both experiments originated from the same stock culture.

Figure 10:
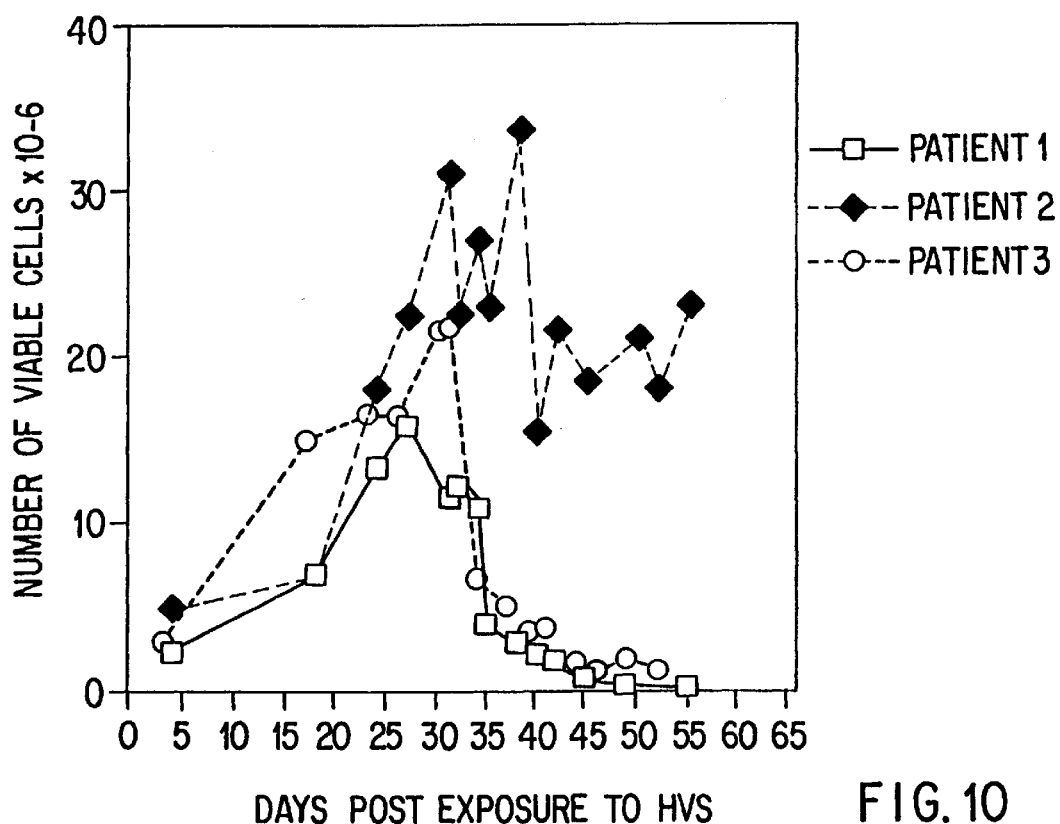

FIG. 10. Establishment of a HVS-transformed CD8+ population. CD8+ cells from three HIV+ patients 1(■), 2(♦), and 3 (○) were exposed to HVS at day 0. Viable cell numbers as measured by erythrosin red dye exclusion are shown over the course of 57 days.

Figure 11:
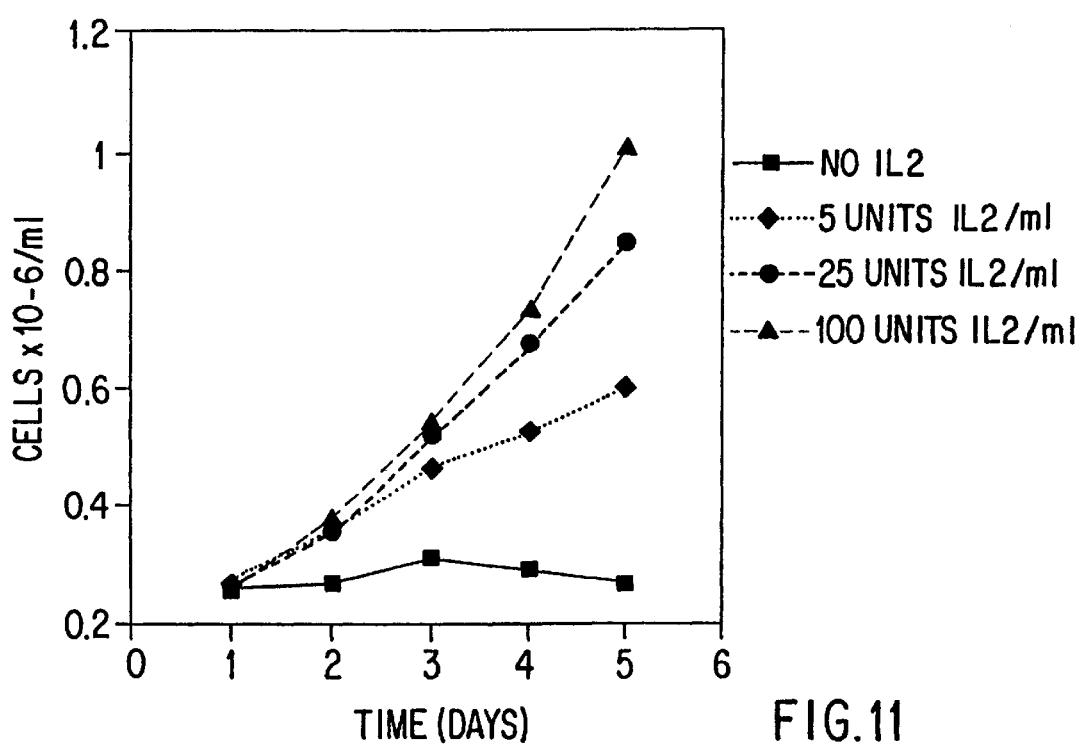

FIG. 11. IL-2-dependence of the HVS-transformed CD8+ cells. The cells were cultured in the presence of 0 (■), 5 (♦), 25 (●), and 100 ( ) units of recombinant IL2/ml of AIM-V medium (unsupplemented with FCS). Viable cell numbers were ascertained at daily intervals.

Figure 12:
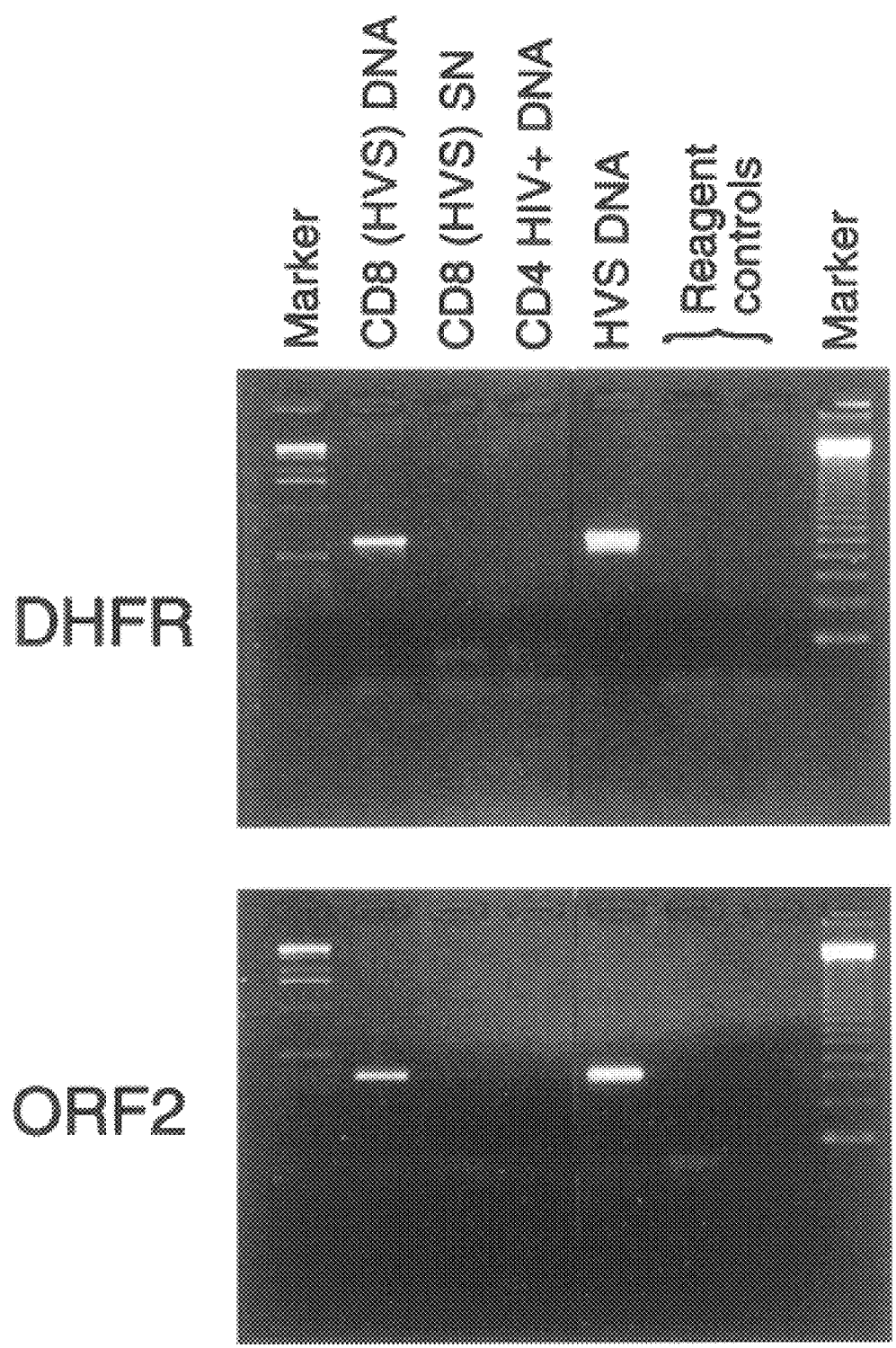

FIG. 12. Detection of HVS DNA sequences in the transformed bulk CD8+ population using the polymerase chain reaction. In the upper panel primers corresponding to the HVS dihydrofolate reductase genes were used. In the lower panel the primers were specific for the HVS ORF 2.

Figure 13:
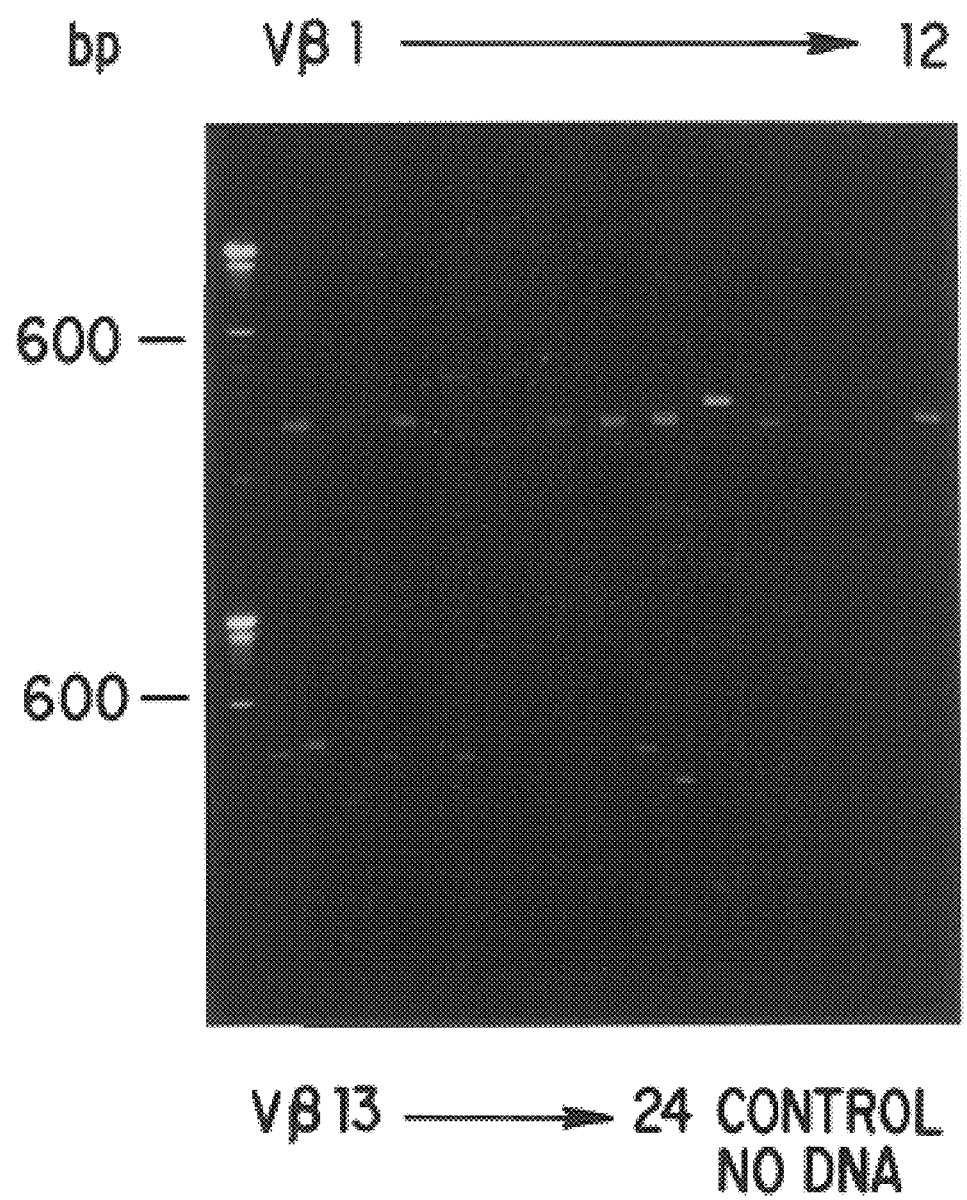

FIG. 13. PCR amplification of the V$\beta$ region of the T-cell receptor genes in the bulk HVS-transformed CD8+ cells from a patient.

Figure 14A:
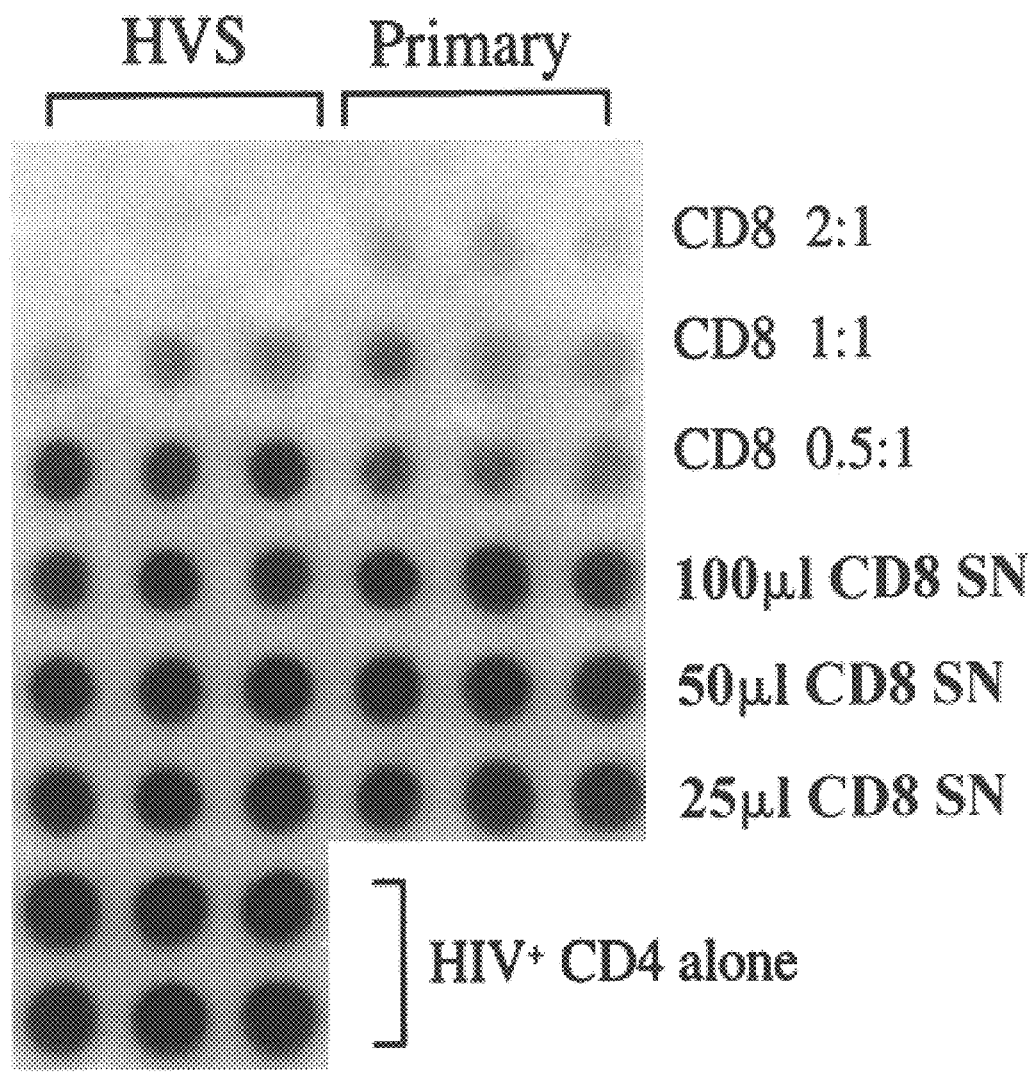
Figure 14B:
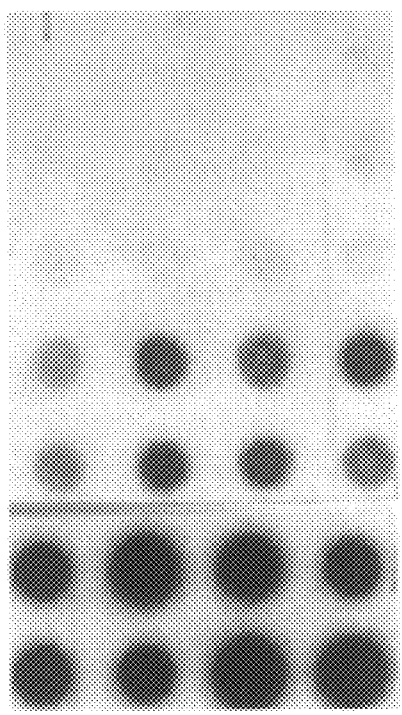

FIG. 14. (A) Comparison of the ability of primary and HVS-transformed CD8+ cells to suppress HIV-1 production by CD4 cells from the same patient. The figures represent autoradiographs of DE81 membrane-bound RT assay products corresponding to cell culture supernatants. (B) HVS-transformed CD8+ cells can suppress HIV-1 production by CD4 cells from a MHC-I mismatched patient.

Figure 15A:
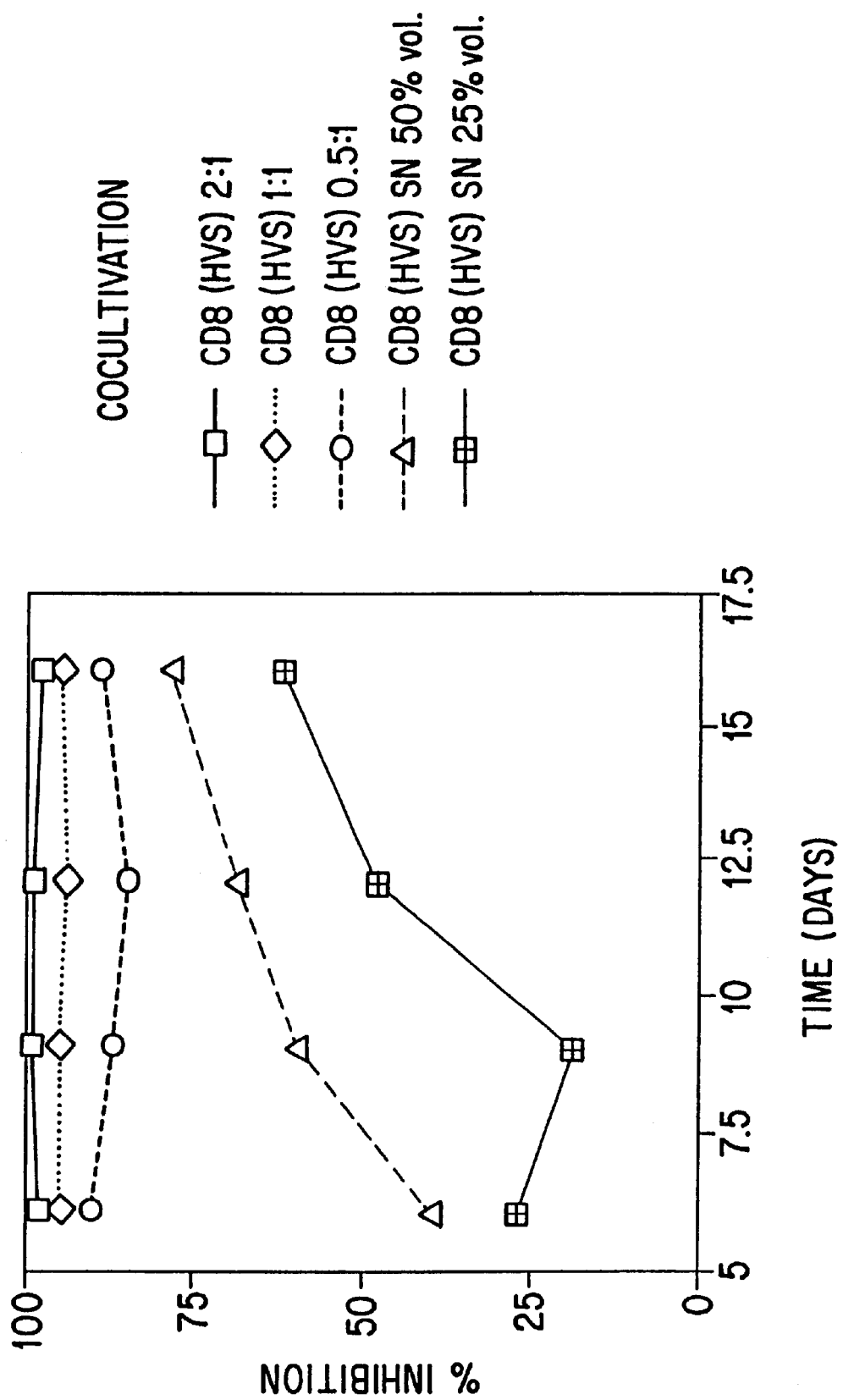
Figure 15B:
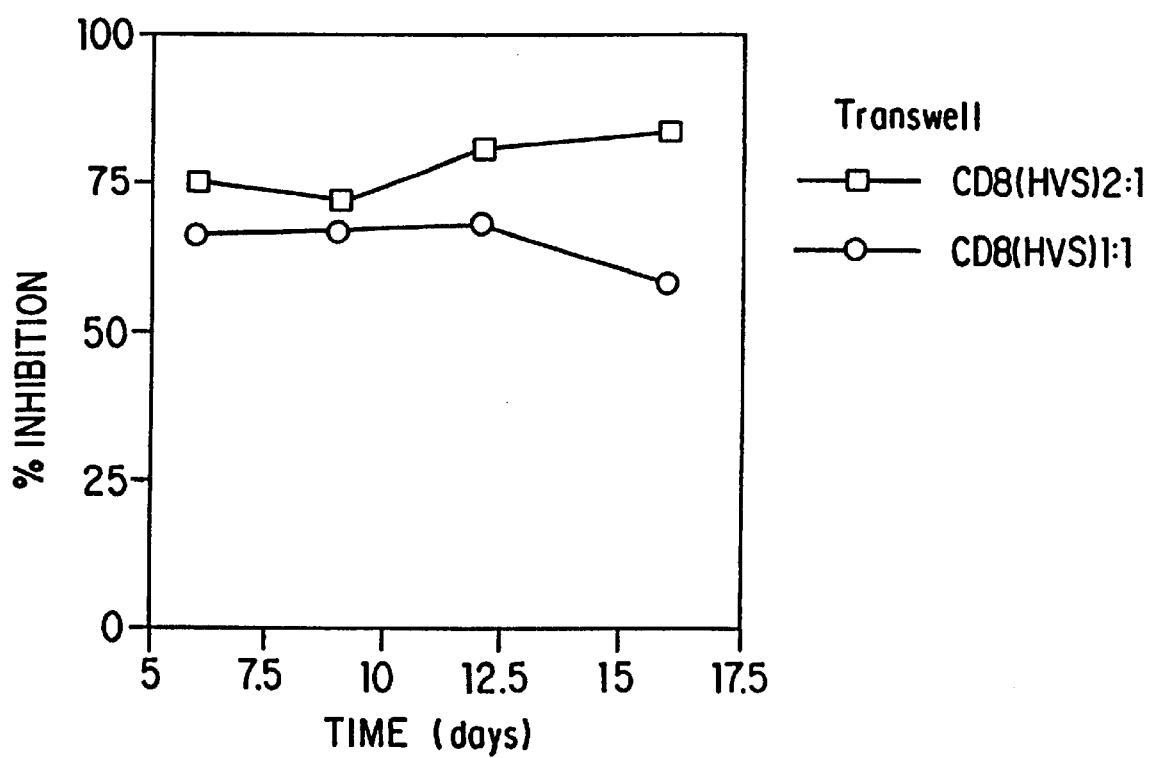

FIG. 15. Comparison of HVS-transformed CD8+ cell inhibition of virus production in transwell and cocultivation assays. (A) Transwell experiment using HIV+ CD4 cells in the upper compartment and HVS-transformed CD8+ cells in the lower compartment at varying ratios to the CD4 cells. (B) A CD4–CD8+ cocultivation assay was performed in parallel using the same preparations of cells utilized for the transwell study. The cultures were sampled at intervals between days 6 and 17. Each point in the cocultivation assay is the average of 3 replicate culture wells.

5. DETAILED DESCRIPTION OF THE INVENTION

The present invention relates to a soluble molecule produced by the CD8+ subclass of T-lymphocytes that is able to inhibit HIV viral replication. The invention further relates to an assay system for detection of the antiviral activity wherein a reporter gene is cloned adjacent to the HIV viral LTR sequences. The development of the assay system is based on the observation that the suppressor molecule inhibits transcription of genes linked to the HIV LTR promoter sequences. In addition, the invention is directed to the isolation of clonal CD8+ cells that expresses the antiviral activity. The invention is further related to the generation of permanently established CD8+ cell lines that express the antiviral activity. Such established cell lines are characterized by their ability to proliferate continuously in tissue. Such cell lines may be advantageously used for purification and characterization of the suppressor molecule and/or for cloning of the CD8+ suppressor molecule. The CD8+ suppressor molecule may be used therapeutically to inhibit HIV-replication.

5.1. CD8+ SUPPRESSOR MOLECULAR INHIBITS HIV-1 VIRAL TRANSCRIPTION

The effect of CD8+ cells on HIV-1 replication was investigated by performing experiments in which CD8+ cells, prepared from HIV-1 infected individuals by immunoaffinity techniques, were mixed with virally infected CD4+ cells in a 2:1 ratio. The inhibition of HIV-1 viral replication can be measured by determining the levels of reverse transcriptase activity in HIV-1 infected cells. As illustrated in FIG. 1, inhibition of viral replication was virtually complete in the presence of CD8+ cells.

Experiments were performed to test whether the mechanism by which the CD8+ suppressor molecule inhibits viral replication is through inhibition of viral gene transcription. A recombinant expression vector was constructed comprising the HIV-1 LTR promoter sequences cloned adjacent to the CAT reporter gene (FIG. 2). The construct was co-transfected into affinity purified CD4+ cells with a second construct expressing the product of the viral Tat gene which is required for viral transcription. A construct consisting of the CAT gene cloned adjacent to the cytomegalovirus immediate early promoter (CMV-IE, FIG. 2) was used as a control (FIG. 2). As indicated in FIG. 3, decreased levels of CAT activity were observed in the presence of autologous $CD8^+$ cells, indicating inhibition of HIV-1 LTR and Tat-mediated HIV-1 LTR transcription in the autologous CD4+ infected cells. Similar experiments were carried out using heterologous $CD8^+$ cells. When these cells were mixed with the transfected CD4 cells a decrease in CAT activity was also observed (FIG. 4) indicating that compatibility at the major histocompatibility locus (MHC) is not required for HIV-1 suppressor activity. In addition, supernatants derived from $CD8^+$ cell culture exhibited inhibitory activity indicating that the antiviral activity is a soluble factor secreted by the $CD8^+$ cells (FIG. 5)

In addition, other viruses of human and animal origin contain similar and/or identical promoter elements as those found in HIV, raising the possibility that the $CD8^+$ suppressor molecule may be of value in the treatment of other viral infections such as CMV, HIV-2, HTLV-1 and 2, FeLV, etc.

5.2. SUBSETS OF $CD8^+$ CELLS EXPRESS ANTI-VIRAL ACTIVITY

The availability of $CD8^+$ cell clones expressing antiviral activity will permit extensive surface marker phenotyping of the cells producing this activity. Once the distinguishing phenotype(s) of these cells is established, improved immunoaffinity techniques for purifying these cells can be devised. If these cells play a role in maintaining the asymptomatic state during HIV infection, these markers may be useful for a) clinical staging of infected individuals, b) monitoring the effect of antiviral therapy on disease progression, c) monitoring the effectiveness of therapy with immunological/biological response modifiers, and d) monitoring vaccine response.

Such cell lines may also be used for purification and characterization of the suppressor molecule using methods and techniques described in Section 5.3., infra. The cell lines may also be used as a source of RNA from which cDNA libraries may be constructed as described in Section 5.4., infra.

In a specific embodiment, described herein, $CD8^+$ cells were immunoaffinity purified from the blood of an HIV infected patient and the purified $CD8^+$ cells were subjected to limited dilution cloning. The resulting $CD8^+$ primary cell clones were assessed for their ability to inhibit tat-mediated HIV LTR transcription in autologolous B-lymphocytes cell lines transfected with the tat encoding vector and the LTR/CAT expression vector. FIG. 6 shows the level of CAT inhibition observed for three $CD8^+$ primary cell clones. As indicated in the Figure, the clones exhibit varying degrees of inhibition of transcription. Clone 2 (DU. HL-1) shows the greatest inhibition of CAT activity while clone 4 (DU. HL-4) does not inhibit activity.

As lymphocytes proliferate and differentiate they express cell surface markers which may be used to identify the different classes of lymphocytes present in the body. The different classes of lymphocytes may be sorted based on the differential expression of cell surface markers using antibodies directed to those cell surface markers and flow cytometry. In yet another embodiment of the invention, described herein, flow cytometry was used to measure cell surface markers expressed on the cell surface of clonal populations of $CD8^+$ cells derived from asymptomatic HIV-1 infected patients. The clonal cell lines from each of the individual patients varied in their ability to inhibit HIV replication. As indicated in TABLE I a variety of phenotypic markers are displayed within the suppressive and non-suppressive clonal populations. The suppressive clones tended to express activation markers such as HLA-DR, S6FI, CD25 and CD28 to a much higher degree than non-suppressive clones.

TABLE I

| Phenotypic | Clone | | | | | |
| | Non-Suppressive | | Suppressive | | | |
| Marker | B5.5 | B18 | B6 | B11 | B22.5 | S92 |
|---|---|---|---|---|---|---|
| HLA-DR | 14% | 25% | 13% | 82% | 47% | 72% |
| CD25 | 4% | 17% | 58% | 58% | 16% | 40% |
| CD38 | 4% | 65% | 67% | 90% | 61% | 76% |
| CD28 | 0% | 41% | 64% | 35% | 37% | 16% |
| CD45RA | ND | 5% | 4% | 19% | ND | 34% |
| CD45RO | ND | 45% | 67% | 82% | ND | 65% |
| S6F1 | 23% | 16% | 14% | 59% | 56% | 57% |
| CD57 | ND | 0% | 2% | 0% | ND | 10% |
| TcR (Vβ) | 5.1 | 1 | 5.1 | 12 | ND | 13 |

The increased expression of specific cell surface markers on $CD8^+$ cells expressing antiviral activity will permit the use of improved immunoaffinity techniques for purifying these cells.

5.3. GENERATION OF $CD8^+$ PERMANENTLY ESTABLISHED CELL LINES THAT EXPRESS ANTI-VIRAL ACTIVITY

Cultures of normal lymphocytes tend to stop growing after a finite number of generations. Permanent lymphocyte cell lines may be generated by the transfer of genetic information encoding cellular or virally derived oncogenes. The transfer and stable uptake of such oncogenes into the genome of purified lymphocytes will confer on those transformed cells the ability to proliferate continuously in tissue culture.

In an embodiment of the invention permanent $CD8^+$ cells lines were generated by preparing $CD8^+$ cells from HIV+ patients and exposing the purified $CD8^+$ cells to *Herpesvirus saimiri*. One particular transformed culture, acquired from patient 2 and designated DU.WS-1-CD8 (HVS), was chosen for further analysis. As demonstrated in FIG. 12, DU.WS-1-CD8 (HVS) cells contained HSV DNA integrated into their genome as indicated by detection of polymerase chain reaction products of the predicted size. In addition, as presented in FIG. 14 the transformed $CD8^+$ cells were as potent as primary $CD8^+$ cells in their ability to inhibit HIV-1 replication in HIV-infected CD4 cells. The results presented in FIG. 15 demonstrate that the transformed $CD8^+$ cells produce an inhibitory activity mediated by a soluble factor capable of passing through a membrane.

In an embodiment of the invention permanently established $CD8^+$ transformed cell lines may be generated using a variety of methods. For example, $CD8^+$ cells prepared from HIV+ patients may be transfected with cellular oncogenes such as, for example, ras, src, fos and myc. Alternatively, the $CD8^+$ cells may be transfected with oncogenic viral genes such as EIA of adenovirus, large T of SV40 or middle T of polyoma virus. Additionally, purified $CD8^+$ cells may be infected with various transforming viruses such as Herpes, SV40 or adenovirus.

Once permanently established cell lines are obtained, they may be subjected to limited dilution cloning. The resulting cell clones may be assessed for their ability to produce the CD8 suppressor molecule.

The permanently established cell lines of the invention are defined as those CD8+ cells producing antiviral activity and those cells capable of continuous proliferation and propagation in tissue culture. The availability of such transformed cell lines that produce anti-viral activity will facilitate the purification and characterization of the CD8+ suppressor molecule.

5.4. PURIFICATION AND CHARACTERIZATION OF CD8+ SUPPRESSOR MOLECULE

The CD8+ suppressor molecule is secreted by CD8+ cells. In addition, primary cell clones expressing the antiviral activity have been isolated (see Section 5.2., supra). The CD8+ antiviral activity may be isolated from the conditioned media of such cells and subsequently purified to high specific activity. Purification of the CD8+ suppressor molecule may be achieved utilizing various procedures and techniques known in the art which include but are not limited to chromatography (e.g., reverse phase liquid, gel permeation, liquid exchange, ion exchange, size exclusion, affinity chromatography), centrifugation, electrophoretic procedures, differential solubility, or by any other standard technique for the purification of proteins.

During any protein purification process, the success of the process depends on the availability of a reliable assay system for measuring the presence of the protein of interest. In an embodiment of the invention, inhibition of HIVI-LTR and/or Tat dependent HIV transcription may used as an indicator of CD8+ suppressor activity. For example, a recombinant expression vector may be engineered to contain the HIV LTR promoter sequences cloned adjacent to a reporter gene and suppressor activity may be measured by assaying for reporter gene activity. Reporter genes that may be used include, but are not limited to those encoding chloramphenicol acetyltransferase (CAT), firefly luciferase or human growth hormone. In the assay system described here, the LTR/reporter gene constructs are co-transfected into an appropriate cell line using transfection methods such as, for example, calcium phosphate transfection, DEAE-dextran transfection, electroporation or liposome-mediated transfection. The transfected cells may then be used to test for the presence of antiviral activity. In a specific embodiment described herein, the HIV-LTR sequences were cloned adjacent to the CAT gene, the construct was transfected into infected CD4 cells and the presence of CD8+ antiviral activity was determined by measuring CAT activity (FIG. 3 and FIG. 4).

Using standard techniques for protein purification and the assay system described above, the CD8+ suppressor protein may be purified to homogeneity. Once purified, the CD8+ protein may be subjected to microsequencing, using techniques routinely used by those skilled in the art to determine the amino acid sequence of a protein (see, Current Protocols in Molecular Biology, Ausubel et al., Green Publishing Associates and Wiley Intersciences, N.Y.) If the CD8+ suppressor molecule is blocked at the amino terminus, the protein may be chemically cleaved or partially enzymatically digested to yield peptide fragments that may be purified and sequenced.

The purified CD8+ protein may be used for production of antibodies to epitopes of the CD8+ protein. Such antibodies include but are not limited to polyclonal and monoclonal antibodies. For production of antibodies, various host animals may be immunized by injection with the CD8+ protein including but not limited to rabbits, mice, rats etc. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and Corynebacterium parvum.

Monoclonal antibodies to CD8+ suppressor molecule may be prepared by using any technique which provides for the production of antibody molecules by continuous cell lines in culture. These include but are not limited to the hybridoma technique originally described by Kohler and Milstein, (Nature, 1975, 256:495–497), the human B-cell hybridoma technique (Kosbor et al., 1983, Immunology Today, 4:72; Cote et al., 1983, Proc. Natl. Acad. Sci., 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used.

Antibody fragments which contain specific binding sites of the CD8+ suppressor molecule may be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments.

Alternatively, Fab expression libraries may be constructed (Huse et al., 1989, Science, 246:1275–1281) to allow rapid and easy identification of monoclonal Fab fragments with the desired specificity to the CD8+ suppressor molecule.

5.5. CLONING OF CD8+ SUPPRESSOR MOLECULE

The present invention relates to methods for cloning of the CD8+ suppressor molecule. Using methods which are well known to those skilled in the art, recombinant cDNA libraries may be constructed using RNA prepared from cells known to express the CD8+ suppressor molecule. The cDNA libraries may be constructed using a variety of vector systems, including but not limited to, bacteriophage vectors, plasmid vectors or mammalian expression vectors. See, for example, the techniques described in Sambrook et al., 1989, Molecular Cloning: A Laboratory Manual, Cold Spring Harbor Laboratory, N.Y. and Current Protocols in Molecular Biology, Green Publishing Associates and Wiley Intersciences, N.Y.

The recombinant cDNA libraries may be screened using a number of different techniques. For example, a mixture of degenerate oligonucleotide probes may be designed utilizing the information derived from protein sequencing of the CD8+ suppressor protein (see Section 5.3 supra). The oligonucleotides may be labeled and used directly to screen a cDNA library for clones containing inserts with sequence homology to the oligonucleotide sequences. Alternatively, the oligonucleotides may be used as primers in a polymerase chain reaction. The template for the reaction is cDNA obtained by reverse transcription of mRNA prepared from cells known to express the suppressor activity. The amplified DNA fragment may be labeled and used to screen a library for isolation of full length clones. In another example, an expression library may be screened immunologically using polyclonal or monoclonal antibodies directed against the CD8$^+$ suppressor molecule. In yet another embodiment of the invention, a cDNA library may be engineered into a mammalian expression vector and screened by transfection into the appropriate mammalian cell line followed by assaying for anti HIV suppressor activity in the tissue culture supernatant.

In a preferred embodiment of the invention, a subtracted cDNA library may be constructed using RNA prepared from expressing and non-expressing clonal CD8$^+$cells. The subtracted library may be screened using the LTR/reporter gene assay system. A subtracted cDNA library contains cDNA clones corresponding to mRNAs present in one cell type ([+] cell type) that are not present in a second cell type ([−] cell type). Construction of this type of library enriches for cDNA clones of interest and is used in the isolation of a cDNA clone corresponding to a particular mRNA where the screening procedure is laborious because a specific DNA sequence or antibody is unavailable.

In an embodiment of the invention a subtractive library may be constructed using mRNA prepared from the expressing [+] and non-expressing [−] clonal CD8$^+$cell lines (see Section 5.2., supra). The [+] cDNA is prepared from cells expressing the antiviral activity and oligonucleotide linkers are ligated onto the ends of the cDNA fragment resulting in endonuclease recognition sites on each end of the cDNA fragment. The [−] cDNA is prepared with blunt ends and digested with a restriction endonuclease that reduces the [−] cDNA fragments to small blunt ended fragments. The [+] cDNA is then mixed with a 50-fold excess of fragmented [−] cDNA, the DNAs are heated to melt apart the double-stranded DNA, and the single stranded DNA is allowed to reanneal. The only [+] cDNA likely to regenerate double stranded fragments with restriction endonuclease restriction sites at each end are those sequences for which no complementary [−] fragments were present. Annealed fragments are ligated in an expression vector having complementary cohesive ends. The resulting cDNA library may be screened using the LTR/CAT expression system.

In yet another embodiment of the invention a method for separating and cloning differentially expressed mRNAs by means of polymerase chain reaction may be used to clone a cDNA coding for the CD8$^+$suppressor molecule (Liang et al., 1992, Science 257:967). Such a method may be utilized using RNA prepared from expressing and non-expressing CD8$^+$ cell lines.

5.6. USES OF THE CD8$^+$ SUPPRESSOR MOLECULE

Currently approved treatments for HIV infection and acquired immunodeficiency disease are pharmaceuticals such as dideoxynucleosides that target viral reverse transcriptase (i.e. AZT, ddl, ddC). Though some clinical benefit has been demonstrated for these agents, drug resistant viral mutants arise limiting their usefulness. Moreover, these agents are only effective against de novo infection and do not exert an antiviral effect against chronically infected or latently infected cells. More effective treatments for HIV infection and AIDS are greatly needed.

The CD8$^+$ subclass of T-lymphocytes produce a molecule that inhibits HIV replication suggesting the potential usefulness of this molecule as a therapeutic for treatment of HIV infection and acquired immunodeficiency disease. Because of the ability of the CD8$^+$ molecule to prevent virus production in cells already infected, it may be of use prophylactically in settings such as vertical transmission of HIV from mother to infant or in acute exposure to HIV. Because the molecule may play a role in maintaining the asymptomatic state of HIV infected individuals, it may be of use for clinical staging of disease progression, monitoring the effects of immune or biological response modifier therapy and for assessing effectiveness of certain vaccination protocols.

6. EXAMPLE: CD8$^+$ SUPPRESSOR ACTIVITY INHIBITS HIV-1 REPLICATION

6.1. MATERIALS AND METHODS

6.1.1. REVERSE TRANSCRIPTASE ASSAYS

Peripheral blood mononuclear cells (PBMC) were prepared from freshly-drawn, anticoagulated blood by standard Ficoll-Hypaque density separation. CD4 and CD8$^+$ lymphocytes were purified by attachment to anti-CD4 and anti-CD8$^+$ microCellector flasks (Applied Immune Sciences) according to the manufacturers recommendations, washed extensively, and cultured for 3 days in medium containing RPMI 1640, 20%, v/v fetal calf serum, 50 U/ml recombinant IL-2 (Hoffmann LaRoche, Inc.) 50 $\mu$g/ml gentamicin sulfate, and 3 $\mu$g/ml phytohemagglutinin (PHA, Sigma, Inc.). Cells were removed from the microCellector flasks, aliquots of the CD4 and CD8$^+$ cell suspensions were analyzed for relative purity by FACS analysis and cell viability was determined by vital dye exclusion. The remaining cell suspensions were cultured for an additional 24 hr in the same medium as above but lacking PHA. CD4 cells were adjusted to 2×10$^6$ cells/ml and 100 $\mu$l aliquots were cultured in duplicate or triplicate wells of 96-well microtitre plate with 100 $\mu$l of fresh medium or 100 $\mu$l of autologous CD8$^+$ cells (adjusted to 4×10$^6$ cells/ml), and cultures were incubated at 37° C. in a humidified CO$_2$ incubator. At 24 hr intervals 100 $\mu$l aliquots of cultures supernatants were taken, adjusted to 1% Triton X-100 and assayed for reverse transcriptase (RT) activity as described below or frozen at −70° C. until assayed. The cultures were fed with 100 $\mu$l of fresh medium each time supernatants were harvested. RT activity was assayed by a modification of the published methods of Goff et al., and Willey et al. 10 $\mu$l of triton lysate was mixed with 50 $\mu$l of a reaction cocktail containing 50 mM Tris-HCl. pH 7.8, 75 mM KCl, 2 mM DTT, 5 mM MgCl$_2$, 5 $\mu$g/ml Poly A, 1.5 $\mu$/ml OligodT$_{12-18}$, 0.05% NP-40, and 10 $\mu$Ci/ml 32P-TTP, and incubated at 37° C. for 90 min. 40–50 $\mu$l aliquots of reaction mixtures were spotted onto either DE-81 paper (Whatmann) or onto NA-45 membranes (Schleicher & Schuell) in a manifold sample filtration manifold (Schleicher & Schuell), and the membranes or paper were washed several times with 2X SSC (0.3M NaCl, 0.03M NaCitrate), followed by 2X SSC containing Bromophenol blue to locate spots. Autoradiography was performed, and the membranes or DE-81 paper counted using a Packard Matrix 9600 Direct Beta Counter. Results presented are the means of duplicate or triplicate wells.

6.1.2. HIV-1 LTR CAT CONSTRUCTS

The plasmids used in these studies were as follows: 1) pLTR 18, constructed by inserting the Xhol-BamHI LTR-CAT containing fragment of pU3RIII (Rosen C A, Sodroski J G, Haseltine Wash., 1985) into pTZ19R (United States Biochemical) at the Hind III site by blunt-end ligation. Expression of the chloramphenicol acetyl transferase (CAT) reporter gene in this vector is under the control of the HIV-1

LTR promoter; 2) pgtat. a tat expression vector under the control of the CMV-IE promoter (Malim M H., Hauber J., Fenrick R., Cullen B R., 1988); 3) pCMVCAT (kindly provided by Dr. B. Cullen, Duke University Medical Center), expression of the CAT reporter gene in this vector is under the control of the same CMV-IE promoter present in the pgtat vector.

6.1.3 TRANSFECTIONS AND CAT ASSAYS

Purified populations of CD4 and CD8+ lymphocytes were prepared from freshly-drawn anticoagulated blood as described in Section 6.1.1., except that purified CD4 and CD8+ cells were expanded in culture for 2–5 days prior to setting up the transfection. To assess effects of CD8+ cells on HIV-1 LTR or CMV-IE transcriptional activity, CD4 lymphocytes ($20 \times 10^6$ cells) were transfected with 10 µg of plasmid (either pLTR 18 or pCMVCAT) by electroporation using a Bio-Rad Gene Pulser. To assess effects on tat-mediated HIV-1 LTR transcription. $20 \times 10^6$ CD4 lymphocytes were transfected by electroporation with 2 µg pgtat and 10 µg pLTR 18. The protocol used for the transfections was previously described by Cann et al. The settings used for electroporation were 960 µF, 250 V for a single pulse. 4 ml aliquots of CD4 cells in fresh medium ($1.25 \times 10^6$ cells/ml) from a single transfection were aliquoted into 4 flasks containing either an equal volume of autologous CD4 cell conditioned medium, an equal volume of autologous CD4 cell conditioned medium containing $10 \times 10^6$ non-transfected autologous CD4 cells, an equal volume of autologous CD8+ cell conditioned medium, or an equal volume of autologous CD8+ cell conditioned medium containing $10 \times 10^6$ autologous CD8+ cells. The volume of each flask was adjusted to 10 ml with a combination of fresh medium (RPMI 1640, 10% heat inactivated fetal calf serum, 5% IL-2 (Cellular Products, Inc.) and 1% Pen-Strep (Gibco)), and either autologous CD4 or CD8+cell conditioned medium so that the final concentration of conditional medium in each flask was 50%. Cultures were incubated for 48 hr at 37° C. in a humidified $CO_2$ incubator. Cultures were harvested, and CAT activity was determined essentially as described by Ballard et al., except that 1% Triton X-100 was added to the cell disruption buffer which contained 100 mM Tris-HCl, pH 7.8. CAT activity was not affected by the presence of 1% Triton X-100. Data are plotted for CAT activity in cultures containing autologous CD8+ cells compared to the activity measured in cultures derived from the same transfection containing autologous CD4 cells. Horizontal lines are drawn to indicate the means of each population. To test tat-mediated transcription in heterologous CD4 cells a flask containing heterologous CD8+ cell conditioned medium and $10 \times 10^6$ heterologous CD8+ cells was substituted in each transfection. Data are plotted for CAT activity in cultures containing autologous or heterologous CD8+ cells compared to the activity measured in cultures derived from the same transfection containing autologous CD4 cells.

CAT activity was measured in conditioned medium removed from cultures containing autologous CD4 cells, cultures containing autologous CD8+ cells and cultures containing autologous CD8+ cells. Each data set from an individual subject was derived from a single transfection. CAT activity is expressed as percent conversion, each assay was based on $5 \times 10^6$ transfected CD4 cells.

6.2. RESULTS

6.2.1. CD8+ CELLS INHIBIT HIV-1 REPLICATION IN CD4 HIV INFECTED CELLS

CD8+ cells prepared from HIV-1 infected individuals by immunoaffinity techniques and stimulated with PHA, inhibit HIV-1 replication in autologous, infected CD4 cells. The potency of the antiviral effect is striking. When CD8+ cells are incubated with CD4 cells in a 2:1 ratio, inhibition of viral replication is virtually complete as measured by reverse transcriptase (FIG. 1).

To investigate the mechanism of CD8+ antiviral activity the effect of CD8+ cells on HIV-1 transcription was examined. Autologous and heterologous PBMC-derived CD4 cells were transfected by electroporation with an HIV-1 LTR CAT construct and a construct that expresses the product of the tat gene. CAT activity was measured in the presence of CD8+ cells and as illustrated in FIGS. 3 and 4, CD8+cells from HIV-1 infected individuals inhibit tat-mediated HIV-1 LTR transcription in autologous and heterologous CD4 cells. Experiments conducted with supernatants derived from CD8+ cell cultures indicate that a significant fraction of the inhibitory activity can be found in the supernatant indicating that the suppressor activity is secreted by CD8+ cells (FIG. 5).

7. EXAMPLE: ISOLATION OF CD8+ CLONAL CELLS EXPRESSING THE ANTI-HIV-1 SUPPRESSOR MOLECULE

7.1. MATERIALS AND METHODS

7.1.1. ESTABLISHMENT OF CD8+ CELL CLONES

Peripheral blood mononuclear cells (PBMC) were prepared from freshly-drawn, anti-coagulated patient blood by standard Ficoll-Hypaque density separation. Twenty million washed PBMC were incubated with anti-CD8+bound magnetic microspheres (Dynal, Inc.) at a bead:cell ratio 10:1 in RPMI 1640+1% FCS. After 45' incubation at 5° C. (with occasional resuspension), CD8+ cell/microsphere conjugates were captured on a rare earth magnet, washed twice, and recaptured. The conjugates were transferred to a T-25 tissue culture flask containing 10 ml of RPMI 1640, 20% v/v fetal calf serum. 50 mg/ml of gentamicin sulfate, 3 mg/ml phytohemagglutinin (PHA: Sigma, Inc.) and 50 U/ml recombinant interleukin 2 (IL-2; Hoffmann LaRoche, Inc.) Conjugates were incubated at 37° C., 5% $CO_2$ for 48 hours, after which the microspheres were removed by magnetic capture. The remaining CD8+ cells in suspension were analyzed for relative purity by FACS analysis and cell viability was determined by vital dye exclusion. Suspensions of $10^2$ viable CD8+ cells were subjected to limited dilution cloning as follows. All wells of a single 96-well round-bottom plate received 10 cells per well, two 96-well plates were seeded at 10 cell/well, and five 96-well plates were seeded at 0.1 cell/well. All wells of all 8 plates subsequently received $2 \times 10^5$ irradiated (6000R) heterologous PMBC feeders in the presence of 200 ng/ml anti-CD3 monoclonal antibody (12F6) and 100 U/ml of IL-2. Plates were incubated at −37° C., 5% $CO_2$. At 14 d intervals, 100 uL of cell-free supernatant was removed and discarded. Wells were re-fed with 100 uL of fresh media containing 20% FCS, 200 ng/ml 12F6, and 100 U/ml IL-2 containing $10^5$ irradiated (6000R) heterologous PMBC feeders. Wells exhibiting macroscopic evidence of cellular proliferation were selected for stepwise expansion into 48-well and 24-well plates and eventually T-25 and T-75 flasks. A 14d re-stimulation cycle was utilized throughout the expansion of the clonal populations of CD8+ cells. Periodic FACS analyses were performed using an extensive marker panel. Twenty-four hours prior to assay, dead feeder cells were removed by Ficoll-Hypaque sedimentation.

7.1.2. ASSAY OF TRANSCRIPTIONAL INHIBITION ACTIVITY IN CD8+ CELL CLONES

CD8+ cells clones were assessed for their ability to inhibit tat-mediated HIV-1 LTR transcription in autologous B lymphocyte cell lines (BLCL) transfected with pgtat and pLTR 18 as follows. Autologous B lymphocyte cell lines were prepared as follows. Peripheral blood was obtained from HIV-1 infected individuals and PBMCs were prepared by Ficoll-Hypaque density gradient separation. Seven to ten million cells were placed in a T-25 flask (Coaster) in 4 ml of cell culture medium (CCM: RPMI 1640, 20% v/v fetal calf serum, 50 µg/ml gentamicin). One ml of EBV supernatant harvested from a marmoset cell line (B95-8; ATCC) and 10 µg of cyclosporin A were added to the cell suspension. The flasks were incubated undisturbed at 37° C. in a humidified $CO_2$ incubator for 3–6 weeks. Once a stably transformed BLCL was established it was resuspended in CCM at a concentration of $3\times10^5$ cells/ml. Routine cell culture maintenance entailed centrifugation and resuspension in new CCM every 2–3 days. In this manner, exponential growth was obtained with cell viability routinely 85–90%. Autologous BLCL were cotransfected with 0.1 µg pgtat/$10^6$ BLCL and 0.5 µg pLTR 18/$10^6$ BLCL as described in the legend to FIG. 2. Transfected BLCL were aliquoted ($1.5\times10^6$ cells) into flasks containing either 50% BLCL conditioned medium, $3\times10^6$ autologous CD8+ cells with 50% autologous CD8+ cell conditioned medium (experiment 1) or $3\times10^6$ heterologous CD8+ cells with 50% heterologous CD8+ cell conditioned medium (experiment 2), or $3\times10^6$ autologous CD8+ clone 2 cells with 50% clone 2 cell conditioned medium, or $3\times10^6$ autologous CD8+ clone 4 cells with 50% clone 4 cell conditioned medium, or $3\times10^5$ autologous CD8+ clone 29 cells with 50% clone 29 cell conditioned medium. The final volume of each culture was adjusted to 10 ml, and cultures were incubated for 48 hr at 7° C. in a humidified $CO^2$ incubator. Cultures were harvested, and CAT activity was assayed as described in the legend to FIG. 2. Data are presented for CAT activity determined in cultures containing CD8+ cells or CD8+ clones compared to cultures only containing transfected BLCL.

7.2. RESULTS

7.2.1 ESTABLISHMENT OF CD8+ CELL CLONES EXPRESSING THE HIV-1 SUPPRESSOR MOLECULE

Peripheral blood mononuclear cells (PBMC) were prepared from a HIV-1 infected blood. CD8+ cells were immunoaffinity purified from the patient's blood and he purified cells were subjected to dilution cloning. The resulting cell clones were assessed for their ability to inhibit HIV-1 LTR transcription in autologous B-lymphocyte cell lines transfected with the HIV-1 LTR CAT and tat encoding constructs. As demonstrated in FIG. 5, the cell clones (clone 2, 4 and 29) vary in their ability to inhibit CAT activity. Clone 2 (DU. HL-2) exhibits the greatest inhibitory activity with clone 4 (DU. HL-4) not inhibiting CAT activity to any significant degree.

8. EXAMPLE: OLIGO CLONAL CD8+ LYMPHOCYTES FROM ASYMPTOMATIC HIV-INFECTED INDIVIDUALS INHIBIT HIV-1 REPLICATION

CD8+ lymphocytes from asymptomatic HIV-1 infected patents are potent suppressors of virus production from infected CD4+ cells. In general, studies of HIV-suppression have been performed in the context of bulk CD8+ cell cultures. Described below are experiments wherein suppression by clonal populations of CD8+ cells cell cultures is demonstrated among the virus suppressive clones derived from an individual patient. A marked heterogeneity between the cells was evident suggesting that CD8+ mediated cell virus suppression is oligoclonal in nature.

8.1 MATERIALS AND METHODS

8.1.1 LYMPHOCYTE ISOLATION

HIV-1 infected asymptomatic volunteers with CD4+ counts >400 were enrolled for this study. Venous blood was obtained under informed consent from all volunteers. Peripheral blood mononuclear cells were prepared from freshly drawn, anticoagulated blood via standard Ficoll-Hypaque density separation. CD8+ and CD4+ lymphocytes were subsequently purified by attachment to anti-CD8+ and CD4+ microCellector T-25 flasks (Applied Immune Sciences, Menlo Park, Calif.) according to manufacturer recommendations. The cells were cultured in the capture flasks with RPMI-1640 medium containing 20% (v/v) fetal calf serum, recombinant interleukin-2 (IL-2) (100 IU/ml) (Hoffmann La Roche, Inc., Nutley, N.J.), and gentamicin sulfate (50 µg/ml). In addition, mitogenic stimulation was accomplished with either phytohemagglutinin (PHA [2 µg/ml]; Sigma, St. Louis, Mo.) for CD4+ targets or a combination of anti-CD3 (12F6[100 ng/ml]; anti-CD28 (100 ng/ml; Becton-Dickinson) antibodies which was used for the CD8+ effector populations.

Cells were cultured for three days at 37° in a humidified $CO^2$ incubator. After harvesting, cell viability generally exceeded 95%. Cell purity of cultures prepared in this manner generally ranged from 87% to 95%, as determined by FACS analysis. Bulk populations were harvested, washed and cultured in the same media (lacking PHA or anti-CD3/CD28) for 3–5 days. CD8+ cells were cloned while CD4+ cells were expanded for use as targets in viral inhibition assays.

8.1.2. CD8+ CELL CLONING

Bulk CD8+ cultures were plated in 96-well plates (Costar, Cambridge Mass.) at a density of 0.5 and 1 cell/well in RPMI-1640 medium containing 20% (v/v) fetal calf serum, recombinant interleukin-2 (100 IU/ml), anti-CD3 (100 ng/ml), anti-CD28 (100 ng/ml) and gentamicin sulfate (50 µg/ml). A total of $1\times10^5$ irradiated (6000 R) allogeneic PBMC/well were added as feeders. Wells with cell growth were expanded in 96 or 48-well plates and restimulated every 10–14 days using the same protocol.

8.1.3 VIRAL SUPPRESSION ASSAY

Duplicate or triplicate 100 µl aliquots of either heterologous or autologous CD4+ cells ($1\times10^6$ cells ml) were added to wells of a 96 well microtitre plate. For acute infection, CD4+ cells from a seronegative MHC mismatched donor were inoculated with approximately $1\times10^4$ $TCID_{50}$ of HIV-$_{LAI}$ (derived from CEM cells) for 1 hour in a 37° C. humidified incubator prior to addition of effectors. For screening assays, approximately $1–4\times10^5$ CD8+ cells, within 72 hours of polyclonal restimulation, were added to the autologous CD4+ targets. In titration experiments, CD8+ clones at the same restimulation interval as in the screening assays were used as effectors against autologous and heterologous CD4+ targets at the following CD8:CD4 ratios: 2.0, 1.0, 0.50, 0.25, 0.12. Transwell experiments were performed in 12 well transwell plates with a membrane pore size of 0.4 μm (Costar). 4×10⁶ CD8⁺ cells per clone were cultured on the bottom well in 2 ml of culture medium. 1×10⁶ acutely infected, heterologous CD4+ cells were cultured in the top chamber in 1 ml of culture medium.

The CD8⁺/CD4+ cell cocultures for both autologous and heterologous assays were incubated for two days. Following the initial two day incubation, 100 μl of supernatant from each well was collected and fresh media was added every other day for the duration of the experiment. For transwell assays, 1 ml from the bottom well and 300 μl from the top well were sampled and replaced with fresh medium. Supernatants harvested from coculture and the top well of the transwell were retained, added to a clean 96 well microtitre plate and mixed with 10 μl per well of a 1% Triton X-100 (Boerhinger Mannheim). Plates were frozen at −70° C. until assayed (within two weeks).

Reverse transcriptase activity was assayed according to the published methods of Goff et al., 1981, J. Virol. 38:239, and Willey et al. 1988, J. Virol. 62:139 as modified by Chen et al., AIDS Res. Hum. Retroviruses 9:107. Briefly, 10 μl of the Triton lysate was mixed with 50 μl of reaction cocktail consisting of 50 mM Tris-HCL (pH 7.8), 75 mM KCI, 2 mM dithiothreitol (DTT), 5 mM $MgCl_2$, poly(rA), oligo $(dT_{2-18})$ [Pharmacia, (1.5 μl/ml)], 0.05% Nonidet P-40 (NP-40)m abd $^{32}$P-TTP (10 μCi/ml), and incubated at 37° C. for 90 minutes. After incubation, 40 μl aliquots were spotted onto DE-81 paper (Whatman, Clifton, N.J.) in a minifold sample filtrations manifold (Schleicher & Schuell, Keene, N.H.), washed several times with 2×SSC (0.3 M NaCl, 0.03 M sodium citrate), followed by 2×SSC containing bromophenol blue to mark the spots. Radioactivity was quantified with a Packard Matrix (Meriden, Conn.) 9600 direct beta counter. Percent inhibition, calculated as [1−(RT ACTIVITY IN CD8⁺CD4+COCULTURE)/(RT ACTIVITY IN CD4+ CULTURE)]×100, was determined over the ten day coculture period.

8.1.4. CYTOFLOURIMETRIC ANALYSIS

To characterize the phenotype of both suppressive and nonsuppressive clones, three color flow cytometric analysis was performed, using different mixtures of monoclonal antibodies. Cytostat MoIgG1-PE/MoIgG2a-FITC, CD450PE/CD 14-FITC, CD8-PE/CD3 FITC (Coulter, Hialeah, Fla.) were used as dual color premixes in combination with Mouse IgG1-PerCP, CD3-PerCP (Becton Dickinson, San Jose, Calif.) respectively, to determine background fluorescence and lymphocyte purity. Additionally, CD45RO-PE, CD45RA-FITC, CD57-PE, CD28-PE, TCRαβ-FITC, CD38-PE, HLA-DR-FITC (Becton Dickenson), IL-2R-PE (CD25), and S6F1-PE (Coulter) were used with CD8-PerCP. From the three color combinations used, percentages for CD8⁺ cells expressing CD45RO+, CD45RA+, CD25+, TCR αβ+, CD38+, HLA-DR+, CD57+, S6F1+, or CD38+/HLA-DR+ were determined by using the dual positive population from the two color histogram of the appropriate dye combinations.

In preparation for flow cytometric analysis, the clones were washed five days after restimulation and incubated for 48 hours in fresh medium. The cells were then washed in 3 ml of Dulbecco's phosphate-buffered solution (PBS) (GIBCO, Grand Island, N.Y.) and resuspended in RPMI (GIBCO) at a concentration of 10⁶ cells/ml. Next, 100 μl of the sample was incubated with 5 μl of the Coulter antibodies (2.5 μl for S6F1) and 10 μl of the Becton Dickinson antibodies in the appropriate combinations for fifteen minutes at room temperature. The samples were washed with 3 ml of PBS, resuspended in 250 μl of PBS containing 1% paraformaldehyde, and held at 4° C. in the dark until analysis was performed on a Coulter EPICS Profile II.

8.2 RESULTS

8.2.1. CLONAL SUPPRESSION OF RT PRODUCTION

The cloning strategy employed for these studies involved initial capture of CD8⁺ cells from patient PBMC, followed by plating 0.5 or 1 cell per well in 96-well plates. The overall cloning efficiency ranged from 50–60%. Fifty to seventy-five positive growth wells were randomly selected for the screening assays of viral suppression.

Some CD8⁺ clones derived from three patients exhibited strong antiviral activity against autologous and heterologous CD4+ lymphocytes. FIG. 7 is a composite showing the effects of representative clones from a typical screening assay. Clones varied in their ability to affect HIV replication. For example, some clones in culture with autologous naturally infected CD4+ cells as well as heterologous naturally or acutely infected CD4+ cells, reduced RT production 95–99% (i.e. S8, B11, and R59), while other clones had little or no effect on RT production (i.e. S6A, B18, R62). Clone B6 was intermediate in the screening assay with inhibition of 65%.

Our routine screening assays examine viral suppression at a single time point on either day 4,6, or 8 of culture. However, the suppressive effect can extend throughout a ten day culture interval. FIG. 8 is a composite of the original radiographic data from the micro RT assays for two representative clones as well as acutely infected CD4+ cells alone over the course of a 10-day cocultivation period. Significant suppression of RT signal by clone B11 is evident throughout the assay period while the nonsuppressive B18clone is devoid of suppressive activity.

Of the clones routinely selected from screening, approximately 20% were capable of inhibiting RT activity by 75% or greater, whereas only 4% showed greater than 90% RT inhibition. After screening, clones were extensively evaluated for as long as they could be maintained in culture.

8.2.2. CLONAL SUPPRESSION IN TRANSWELL

Further evidence to support a soluble factor based and non-cytolytic mechanism of HIV suppression by the clones was obtained with transwell culture vessels which separated cell populations by a 0.4 μM pore-size filter. When CD8⁺ clones were physically separated from infected CD4+ cells, the hierarchy of suppressive ability among the clones was maintained. The addition of the suppressive clone B11 (4×10⁶ cells) to the bottom well of the culture vessel resulted in significant virus suppression of acutely infected CD4+ cells (1×10⁶ cells) in the top well (FIG. 9). Conversely, clone B18 showed little inhibition of virus replication in the same experiment (FIG. 9). A coculture experiment was run in parallel with the transwell experiment. A similar pattern of suppression was evident although suppression was consistently more potent in the coculture assays.

8.2.3. EXPRESSION OF CELL SURFACE MARKERS

To more clearly define the subsets of CD8⁺ cells which were capable of virus suppression, we used dual-color flow cytometry to measure surface antigens and RT-PCR to determine the TcR-Vβ expression. The FACS analyses and aforementioned cytokine analyses were performed on the clones at equivalent times in their activation cycle. Moreover, the day when these analyses were performed corresponds to the day the functional suppression analysis was begun. Thus, minor differences appearing among individual clones are not due to differences in the post-activation intervals.

A summary of cell surface marker expression on subsets of $CD8^+$ cells is as follows:

Almost all of the clones expressed elevated levels (>45%) of CD45RO and CD38 but reduced levels (<35%) of CD57 and CD45RA. Expression of the activation markers (HLA-DR, S6F1, CD25, and CD28) appeared highly variable. Expression of the activation markers HLA-DR and S6F1 was significantly higher in the three most suppressive clones, B11, B22.5 and S92, than in clone B6. CD25 expression was elevated (>40%) in three of the four suppressive clones. Also, CD28 expression was higher in clone B6 (64%) than in B11 (35%), B22.5 (37%), and S92(16%). Furthermore, B5.5 and B18expressed reduced (<25%) levels of HLA-DR, S6F1 and CD25. These data indicated that a diversity of phenotypic activation markers are displayed within the suppressive and nonsuppressive clonal populations with suppressive clones tending to express activation markers to a much higher degree than nonsuppressive clones. The phenotypes have remained stable for at least three months in culture.

In addition to activation marker screening, the Vβ region of the TCR was analyzed to check for both clonality and possible TCR repertoire restriction.

Indeed, each clone possessed a single Vβ—indicative of a bona fide clone. The variability in Vβ type indicated that there was no clear pattern of Vβ expression among the clones that correlated with suppressive activity. The only Vβ type which was expressed in more than one clone, 5.1, appeared in both a suppressive (B6) and a nonsuppressive (B5.5) clone. It should also be noted that 4 of the typed clones were from the same individual and no Vβ trends were observed. Collectively, these Vβ and phenotypic data indicate that these $CD8^+$ clones with antiviral activity are phenotypically heterogeneous and do not belong to a specific $CD8^+$ cell subset.

9. EXAMPLE: GENERATION OF TRANSFORMED $CD8^+$ SUPPRESSOR $CD8^+$ CELLS

9.1. MATERIALS AND METHODS

9.1.1. PREPARATION OF $CD8^+$ CELLS

Venous blood was obtained from asymptomatic HIV+ patients who had been infected for >7 years. PBMCs were prepared by standard Ficoll-Hypaque density separation. $CD8^+$ cells were purified by capture on anti-$CD8^+$ micro-Cellector flasks (Applied Immune Sciences) according to the manufacturer's recommendations, and cultured for 3 days in RPMI 1640 medium supplemented with 10% foetal calf serum, 20 units/ml recombinant interleukin 2 (rIL2), penicillin and streptomycin, and 1 µ/ml phytohaemagglutinin (PHA) at 37° C. in a humidified incubator.

9.1.2. TRANSFORMATION OF $CD8^+$ CELLS WITH HVS

Three days after PHA activation $2.5 \times 10^7$ $CD8^+$ cells from each patient were resuspended at $2 \times 10^6$/ml in RPMI 1640 medium supplemented with 20% foetal calf serum, 20 units/ml recombinant IL2, penicillin and streptomycin. An equal volume of HVS 488-77 stock was added to an M.O.I of 0.5. The cultures were maintained at 37° C. in a gassed $CO^2$ incubator with as little disturbance as possible, refeeding when necessary with fresh medium. After 1 month the viability as measured by erythrosin red dye exclusion had fallen to 30%. At this point viable cells were recovered by Ficoll-Hypaque separation. The removal of dead cells was repeated as necessary over the following 4 weeks, by which time a transformed growth phenotype was evident.

9.1.3 VIRUS SUPPRESSION ASSAYS

Virus suppression assays were performed essentially as previously described by Chen et al. 1993, AIDS Res. and Hum. Retrovir. 9. CD4 target cells were prepared from asymptomatic HIV+ patients using CD4 microcellector flasks and were further depleted of $CD8^+$ cells by using anti-$CD8^+$ antibody coated magnetic beads (Dynal). These CD4 cells were cultured at $2 \times 10^6$/ml in 100 µl aliquots in 96 well plates. $CD8^+$ cells or supernatants from $CD8^+$ cell cultures were added at varying ratios to a final volume of 200 µl. The medium used throughout was AIM-V medium supplemented with 20% fetal calf serum, 20 units/ml recombinant IL2, penicillin and streptomycin. The plates were incubated at 37° C. in a gassed, humidified incubator. At each sampling time point 80 µl of SN was removed, adjusted to 1% Triton X100, and assayed for reverse transcriptase activity. The RT assay method has been described previously (Goff et al., 1981, J. Virol. 38:239–248; Willey et al. 1988, J. Virol. 62:139–147, Chen et al. 1993, AIDS Res. and Hum. Retrovir. 9). After sampling, the cultures were refed with fresh medium or with conditioned supernatant mixed with fresh medium so as to maintain the original assay conditions. Some of these assays were performed using the Transwell system (Costar) in which typically the $CD8^+$ effector cells were seeded in 1.5 mls of medium into the bottom compartment of a 24-well culture plate, and the CD4 target cells were added to the upper compartment in 500 µl. Sampling was performed from the top compartment as described above, but refeeding was additionally done at this time by removing 1 ml of medium from the lower $CD8^+$ compartment, and replacing with 1 ml of fresh medium.

9.1.4. PCR ANALYSIS OF HVS SEQUENCES

Total DNA was extracted from $1 \times 10^6$ HVS-transformed $CD8^+$ cells and from untransformed HIV+ CD4 cells by standard phenol/chloroform extraction. DNA equivalent to $3 \times 10^4$ cells was used as the target in PCR reactions employing the following oligonucleotide primer pairs: For the HVS dihydrofolate reductase gene; 5' GAGAGCTCAAAATCAT-AACTAGCT 3' (nucleotides 4057–4080 in the HVS genome (Biesinger et al. 1990) and 5' GGTTCTTTTGCTAAACT-GTATTGTTGCTG 3' (4664–4692). For the HVS ORF2 GENE; 5' AGTTCCACACAACTAACTACTAGATGAGAT 3' (1061–1089) and 5' ATGGCAAGCGAACCGAAC-CTAAGATATCCA 3' (1412–1441). The PCR reactions contained 50 mM KCl, 10 mM Tris-HCl pH8.3, 1.5 mM $MgCl_2$, 100 µM of each of dCTP, dGTP, dATP and dTTP, 2.5 ng of each primer, and 2.5 units of Amplitaq DNA polymerase in a total volume of 100 µl. The thermal cycling conditions were 6 minutes at 95° C., 30 seconds at 45° C., and 3 minutes at 72° C., The PCR products were analyzed on agarose gels containing ethidium bromide.

9.1.5. MHC-RESTRICTED CELLULAR CYTOTOXICITY

The presence of $CD8^+$ cytoxic lymphocytes among the immortalized cells was detected by standard $^{51}$Cr release assay. Autologous Epstein-Barr virus immortalized B lymphocytes (BLCL) were used as target cells after infection with recombinant vaccinia-HIV constructs. Briefly 1×10$^6$ BLCLs were infected (multiplicity of infection=5:1) for 90 minutes at 37° C. with the following recombinant viruses expressing the *E. coli* lac operon, and the Env, Gag, Pol, and Nef antigens of the HTLV-111B isolate, respectively: vSC8 (Chakrabarti et al. 1985, Mol. Cell. Biol. 5:3403–3409), vPE16 (Earl et al. 1990, J. Virol. 64:2448–2451), vDK1, vCF21 (Flexner et al. 1988, Virol. 166:339–349) and vP1218. Cells were radiolabeled with 100–200 nCi of sodium chromate ($^{51}$Cr; DuPont, Wilmington, Del.) for 16 hours at 37° and 5% $CO_2$. The cells were subsequently washed, counted and plated at a concentration of 5×10$^3$ viable cells/well plate. HVS-immortalized CD8$^+$ lymphocytes were used as effectors at the E:T ratios of 100 and 50:1; each E:T was tested in triplicate. Targets plus medium or 0.5% Triton X-100 were used as control for spontaneous (SR) and maximum release (MR) respectively in 4 hour-assay. The percentage of specific lysis (% SL) was calculated according to the formula [(cpm experimental release) minus (cpm SR)]/[(cpm SR)]×100. Spontaneous release did not exceed 20% MR.

The presence of anti-HIV CTL activity was defined as positive if the % SL against BLCL expressing HIV antigens was 10% higher than the % SL against the control.

9.1.6. CLONING OF CD8$^+$ (HVS) CELLS

The bulk transformed CD8$^+$ cells were resuspended in fresh culture medium (AIM-V medium supplemented with 20% foetal calf serum, 20 units/ml recombinant IL2, penicillin and streptomycin) in a 15 ml tube and left to stand for 1 hour to allow cell aggregates to sediment. The cell suspension was then counted and diluted before plating in 96-well culture dishes at 0.25 cells per well. 5×10$^3$ irradiated PBMCs were added to each well as feeders. The cultures were fed at weekly intervals with fresh medium and expanded as necessary.

9.2. RESULTS

9.2.1. ESTABLISHMENT OF TRANSFORMED CD8$^+$ CELL POPULATIONS

We prepared CD8$^+$ cells were prepared from several asymptomatic HIV+ patients, activated with PHA for 3 days and then exposed to HVS. After approximately 30 days we observed cessation of cell growth and a rapid decline in cell viability in some of our cultures (patients 1 and 3). In another culture (patient 2) we observed continuous activation-independent growth against a background of cell death, consistent with the expansion of a transformed subpopulation (FIG. 10). All the studies described in this work were conducted using later passages of the transformed culture from patient 2. The growth properties of this culture were examined by seeding 5×10$^6$ cells into 10 mls of AIM-V medium (unsupplemented with FCS), containing varying concentrations of rIL2 for approximately 60 hours (FIG. 11). The growth of this population declines if it is moved to serum free medium for extended periods of time (>3 weeks). The experimental results described in the following sections were performed on later passages of the transformed culture from patient 2.

9.2.2 DETECTION OF HVS DNA SEQUENCES IN TRANSFORMED CD8$^+$ CELLS

Total cell DNA was prepared from the CD8$^+$ (HVS) cells 60 days after exposure to HVS and PCR was performed using primers corresponding to the viral dihydrofolate reductase gene and to ORF-2. The latter, also designated STP-C488, has been reported to have transforming and tumor-inducing activity and to be responsible for the viral transforming phenotype (Jung et al. 1991, Proc. Natl. Acad. Sci. USA 89:7051–7055). We obtained PCR products of the predicted sizes using the DNA from the transformed cells as a target (FIG. 12). When we used an extract prepared from the conditioned medium used to cultivate these transformed cells we saw no HVS PCR signals, indicating that no virus-associated DNA was present in the medium. This correlates with findings that when this cell-free conditioned medium was used to overlay a HVS-susceptible monolayer of OMK cells for extended periods no viral CPE or plaque formation is observed. We obtained an upper limit for infections HVS of less than 0.1 pfu/ml. These observations, taken together, indicate that the transformed cells stably contain HVS DNA sequences, but that no infectious virus is being secreted by these cells.

9.2.3. TRANSFORMED CD8$^+$ CELLS ARE POLYCLONAL AND ACTIVATED

We prepared RNA from the CD8$^+$ (HVS) cells, synthesized cDNA and analyzed the DNA this using PCR primers corresponding to the $V_\beta$ region of the T-cell receptor gene. We found that 22 of the 24 $V_\beta$ families were represented in the bulk population (FIG. 13), indicating that our transformed CD8$^+$ culture is polyclonal. We also analyzed the surface marker phenotypes by fluorescence activated cell sorting (FACS) and found that the predominant markers were: CD8, CD25, CD38, S6F1, CD45RO, CD28 and HLA-DR. No CD4 expression was detectable in the population by FACS analysis. The CD25, CD38 and HLA-DR markers are all typical of activated T-cells, the CD25 molecule being the IL-2 receptor. The presence of this marker on the surface of the majority of the cells may correlate with our observation of an IL2-dependent growth phenotype. The CD45RO surface marker indicates that the population is primarily comprised of memory cells.

9.2.4. TRANSFORMED CD8$^+$ CELLS DO NOT EXHIBIT CTL ACTIVITY

To ascertain whether the CD8$^+$ (HVS) cells contained a significant CTL subpopulation four hour [$^{51}$Cr] release CTL assays were conducted employing as targets EBV transformed BLCL cells infected with vaccinia constructs expressing the HIV-1 env, gag, pol and nef proteins as targets. Despite using a high ratio of effector to target cells, we observed no significant HLA-restricted cytolysis compared to the vaccinia vector control.

9.2.5. TRANSFORMED CD8$^+$ CELLS SECRETE A SOLUBLE FACTOR THAT INHIBITS HIV-1 REPLICATION

To compare the inhibitory activity of the HVS-transformed CD8$^+$ cells with that of primary CD8$^+$ cells from the same patient, autologous suppression assays were set up by isolating CD4 cells from the patient and then cocultivating them with the CD8$^+$ cells at defined ratios. The culture supernatants were sampled at regular intervals and assayed for reverse transcriptase activity. The results (FIG. 14A) indicated that the transformed CD8$^+$ cells were very similar to the primary CD8+ cells in their ability to inhibit HIV-1 production by the autologous CD4 cells. To test whether this observed inhibition was MHC class I-restricted a similar assay was performed employing CD4 cells from a completely MHC-I mismatched HIV-1 patient. Inhibition that was a potent as that seen in the autologous assay (FIG. 14B), was observed with the level of suppression with a CD8:CD4 ratio of 2 approaching 98%. These observations, together with the lack of detectable activity in the CTL assays, indicates that the observed inhibition is not due to MHC-I restricted CTL activity.

A transwell assay system in which the effector cells are separated from the target cells by an 0.4 μm membrane was used to investigate whether the inhibition of virus production by HIV-I infected CD4 cells requires cell-to-cell contact. The results from this assay (FIG. 15) indicate that, while the most potent suppression is seen with cocultivation, at least part of the inhibitory activity is mediated by a soluble factor capable of passing through the membrane. In addition, experimental results indicated that the conditioned medium from the transformed CD8$^+$ cells can inhibit virus production by the infected CD4 cells. The level of inhibition seen is comparable to that in the transwell experiments. Of note is the observation that the degree of inhibition increased during the course of the experiment. This may be due to the fact that the cultures were refed with more conditioned CD8$^+$ supernatant at each time of sampling.

10. DEPOSIT OF MICROORGANISMS

The following microorganisms have been deposited with the American Type Culture Collection, (ATCC), Rockville, Md. and have been assigned the following accession numbers:

| Microorganism | Date of Deposit | Accession No. |
|---|---|---|
| DU. HL-2 | Mar. 26, 1993 | CRL 11310 |
| DU. HL-4 | Mar. 26, 1993 | CRL 11309 |
| DU. WS-1-CD8 (HVS) | Jun. 6, 1995 | |

The present invention is not to be limited in scope by the microorganisms deposited since the deposited embodiments are intended as illustrations of single aspects of the invention and any microorganisms which are functionally equivalent are within the scope of the invention.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

It is also to be understood that all base pair sizes given for nucleotides are approximate and are used for purposes of description.

What is claimed is:

1. A method for detecting a CD8$^+$ suppressor molecule that has anti-HIV activity, comprising:

(a) contacting a culture of cells with a sample containing a suppressor molecule,
  (i) wherein the culture of cells comprises cells genetically engineered to contain recombinant DNA expression vector in which a reporter gene is operatively associated with an HIV LTR promoter sequence, and
  (ii) wherein the sample containing the CD8$^+$ suppressor molecule comprises culture supernatant from CD8$^+$ cells or conditioned medium from CD8$^+$ cells; and (b) measuring the inhibition of reporter gene activity, wherein inhibition of reporter gene activity correlates with anti-HIV activity.

* * * * *